US012390485B2

(12) United States Patent
de la Cruz et al.

(10) Patent No.: US 12,390,485 B2
(45) Date of Patent: Aug. 19, 2025

(54) COMPOUNDS AND METHODS FOR SUPPRESSING AN IMMUNE RESPONSE TO SUBSTANCES CONTAINING POLYETHYLENE GLYCOL

(71) Applicant: aAb Therapeutics, LLC, Spring City, PA (US)

(72) Inventors: Vidal F. de la Cruz, Phoenixville, PA (US); Joseph M. Salvino, Chester Springs, PA (US)

(73) Assignee: aAb Therapeutics, LLC, Spring City, PA (US)

( * ) Notice: Subject to any disclaimer, the term of this patent is extended or adjusted under 35 U.S.C. 154(b) by 0 days.

(21) Appl. No.: 17/991,925

(22) Filed: Nov. 22, 2022

(65) Prior Publication Data

US 2023/0102212 A1    Mar. 30, 2023

Related U.S. Application Data

(63) Continuation of application No. PCT/IB2021/054460, filed on May 22, 2021.

(60) Provisional application No. 63/029,012, filed on May 22, 2020.

(51) Int. Cl.
| | |
|---|---|
| *A61K 31/721* | (2006.01) |
| *A61K 45/06* | (2006.01) |
| *A61K 47/60* | (2017.01) |
| *A61K 47/61* | (2017.01) |
| *A61P 37/06* | (2006.01) |

(52) U.S. Cl.
CPC .......... *A61K 31/721* (2013.01); *A61K 45/06* (2013.01); *A61K 47/60* (2017.08); *A61K 47/61* (2017.08); *A61P 37/06* (2018.01)

(58) Field of Classification Search
CPC .. A61K 47/61; C08B 37/0012; C08B 37/0021
See application file for complete search history.

(56) References Cited

U.S. PATENT DOCUMENTS

| | | |
|---|---|---|
| 5,126,131 A | 6/1992 | Dintzis |
| 5,370,871 A | 12/1994 | Dintzis |
| 5,599,912 A | 2/1997 | Rodell |
| 6,022,544 A | 2/2000 | Dintzis |
| 6,375,951 B1 | 4/2002 | Dintzis |
| 6,572,867 B1 | 6/2003 | Schwarz |
| 7,998,486 B2 | 8/2011 | Mautino |
| 8,658,159 B2 | 2/2014 | Tu |
| 9,377,454 B2 | 6/2016 | Rosario-Jansen |
| 2017/0043028 A1* | 2/2017 | Ma ............................ C12N 9/16 |
| 2018/0258160 A1 | 9/2018 | Lai |

FOREIGN PATENT DOCUMENTS

| | | |
|---|---|---|
| EP | 0797615 B1 | 1/1999 |
| WO | 2014029012 A1 | 2/2014 |
| WO | 2015007326 A1 | 1/2015 |

OTHER PUBLICATIONS

Lukyanov, A. et al., J. Biomater. Sci. Polymer Edn., "PEGylated dextran as long-circulating pharmaceutical carrier", 2004, vol. 15, No. 5, pp. 621-630 (Year: 2004).*
Mehvar, Reza, Journal of Controlled Release, "Dextrans for targeted and sustained delivery of therapeutic and imaging agents", 2000, vol. 69, pp. 1-25 (Year: 2000).*
Agusti, R. et al., Recent Advances in Biotechnology, "Carbohydrate PEGylation in Chemotherapy", 2016, vol. 3, pp. 60-101 (Year: 2016).*
Hosseinkhani, H. et al., Gene Therapy, "Dextran-spermine polycation: an efficient nonviral vector for in vitro and in vivo gene transfection", 2004, vol. 11, pp. 194-203 (Year: 2004).*
Li, Zhongbo, Dissertation, "Elucidating and Overcoming Anti-PEG Antibodies to PEGylated Therapeutics and Nanomedicine", 2024 (Year: 2024).*
International Search Report issued Oct. 6, 2021, in PCT/IB2021/054460, 4pp.
Written Opinion of the International Searching Authority issued Oct. 6, 2021, in PCT/IB2021/054460, 4pp.
Scheper, T. et al., "Aqueous Synthesis of PEGylated Quantum Dots with Increased Colloidal Stability and Reduced Cytotoxicity", Bioconjugate Chem. 2016, 27, 414-426, American Chemical Society; DOI: 10.1021/acs.bioconjchem.5b00491.
Sullenger, B. A. et al. "Anti-PEG Antibodies Inhibit the Anticoagulant Activity of PEGylated Aptamers", Cell Chemical Biology, May 16, 2019, 26, 634-644, e1-e3, Elsevier Ltd.; doi.org/10.1016/j.chembiol.2019.02.001.
Figueiras, A. et al., "Dendrimers as Pharmaceutical Excipients: Synthesis, Properties, Toxicity and Biomedical Applications", Materials, Dec. 21, 2019, 13, 65, 1-31, MDPI; doi:10.3390/ma13010065.
Ciach, T. et al., "Dextran Nanoparticle Synthesis and Properties", PLoS ONE, Jan. 11, 2016, 11(1), 1-17, e0146237. doi:10.1371/journal.pone.0146237.
Dintzis, H. M. et al., "Molecular determinants of immunogenicity: The immunon model of immune response", Proc. Natl. Acad. Sci. USA, Oct. 1976, 73, 10, pp. 3671-3675.
Medintz, I. L. et al., "Functionalizing Nanoparticles with Biological Molecules: Developing Chemistries that Facilitate Nanotechnology", Chem. Rev. 2013, 113, 1904-2074, American Chemical Society; dx.doi.org/10.1021/cr300143v.
Jokerst, J. V. et al., "Nanoparticle PEGylation for imaging and therapy", Nanomedicine (Lond). Jun. 2011, 6(4), 715-728; doi:10.2217/nnm.11.19.
Wenande, E. et al., "Immediate-type hypersensitivity to polyethylene glycols: a review", Clinical & Experimental Allergy, 2016, 46, 907-922, John Wiley & Sons Ltd.; doi: 10.1111/cea.12760.
McSweeney, M. D., "Pre-treatment with high molecular weight free PEG effectively suppresses anti-PEG antibody induction by PEG-liposomes in mice", Journal of Controlled Release, 329, Oct. 7, 2020, 774-781, Elsevier B. V.; doi.org/10.1016/j.jconrel.2020.10.011.

(Continued)

*Primary Examiner* — Bahar Craigo
(74) *Attorney, Agent, or Firm* — COOLEY LLP

(57) ABSTRACT

Compounds, compositions and methods for suppressing an immune response to polyethylene glycol (PEG) are provided.

18 Claims, 12 Drawing Sheets

(56) References Cited

OTHER PUBLICATIONS

Bao, G. et al., "Multifunctional Nanoparticles for Drug Delivery and Molecular Imaging", Annu Rev Biomed Eng., 2013, 15, 253-282; Author manuscript; available in PMC Oct. 13, 2018; doi:10.1146/annurev-bioeng-071812-152409.

Thiruppathi, R. et al., "Nanoparticle Functionalization and Its Potentials for Molecular Imaging", Adv. Sci. 2017, 4, 1600279, 14pp., Wiley-VCH Verlag GmbH & Co. KGaA, Weinheim; DOI: 10.1002/advs.201600279.

Nicolaou, K. C. et al., "The Role of Organic Synthesis in the Emergence and Development of Antibody-Drug Conjugates as Targeted Cancer Therapies", Angew. Chem. Int. Ed. 2019, 58, 11206-11241, Wiley-VCH Verlag GmbH & Co. KGaA, Weinheim; DOI: 10.1002/anie.201903498.

Dai, L. et al., "One-pot facile synthesis of PEGylated superparamagnetic iron oxide nanoparticles for MRI contrast enhancement", Materials Science and Engineering C, 41 (2014) 161-167, Elsevier B. V.; dx.doi.org/10.1016/j.msec.2014.04.041.

Yang, H. et al., "Superelastic and pH-Responsive Degradable Dendrimer Cryogels Prepared by Cryo-aza-Michael Addition Reaction", Nature Scientific Reports, 2018, 8, 7155, 10pp.; DOI:10.1038/s41598-018-25456-y.

Lee, C. et al., "Structural basis of polyethylene glycol recognition by antibody", Journal of Biomedical Science, 2020, 27:12, 13pp., Ministry of Science and Technology, Taiwan; doi.org/10.1186/s12929-019-0589-7.

Yamago, S. et al., "Synthesis of structurally controlled hyperbranched polymers using a monomer having hierarchical reactivity", Nature Communications, 8: 1863, 8pp.; DOI: 10.1038/s41467-017-01838-0.

Kang, D., et al., "Synthesis of Dextran/Methoxy Poly(ethylene glycol) Block Copolymer", Journal of Chemistry, 2013, vol. 2013, Article ID 414185, 7pp., Hindawi Publishing Corporation; dx.doi.org/10.1155/2013/414185.

Kozma et al., "Anti-PEG antibodies: Properties, formation, testing and role in adverse immune reactions to PEGylated nano-biopharmaceuticals," Advanced Drug Delivery Reviews, 2020, vol. 154-155, pp. 163-175.

Zalipsky, "Chemistry of Polyethylene Glycol Conjugates with Biologically Active Molecules," Advanced Drug Delivery Reviews, 1995, 16:157-182.

* cited by examiner

PEG-DEX vs Free PEG

COMPOUNDS AND METHODS FOR SUPPRESSING AN IMMUNE RESPONSE TO SUBSTANCES CONTAINING POLYETHYLENE GLYCOL

RELATED APPLICATIONS

This application claims the benefit of U.S. Application No. 63/029,012, filed May 22, 2020, the entire contents of which are hereby incorporated by reference.

BACKGROUND

Many drugs are modified from their active form for reasons that include extending circulating half-life and decreasing immunogenicity of the drug. One example is the covalent attachment of polyethylene glycol (PEG) to the drug, i.e., PEGylation. There are many marketed drugs that are PEGylated. PEGylation increases the circulating half-life by increasing the apparent hydrodynamic radius of a drug, thus decreasing the kidney's glomerular filtration capacity to eliminate the drug. PEGylation can also minimize immunogenicity of the drug. Decreased antibody responses to the drug moiety have been reported.

The presence of antibodies to PEG (i.e., anti-PEG antibodies, or "APAs") can present problems with drug use. PEG was initially considered to be non-antigenic and non-immunogenic, but animal studies have shown that PEGylated proteins (e.g., uricase, ovalbumin, other agents) can induce antibodies to not only PEG, but to the PEGylated agent. APAs are also induced in some patients receiving PEGylated drug treatment.

APAs are found in individuals with no known exposure to PEGylated drugs, with rates exceeding 40% of the population. This may result from exposure to PEG and PEG-like compounds (e.g., polysorbates and poloxamer polymers) found in commercial products and foods. Such APAs are not without consequence. They can accelerate clearance of a drug from circulation in the blood by increasing excretion, thus negating one benefit to PEGylation and requiring larger doses and/or more frequent administration. They can also enhance uptake of immune complexes by certain cells. APAs can inactivate the biological activity of the drug, as well as induce adverse side effects such as infusion site reactions, urticaria, and anaphylactic shock. Such reactions to PEG have recently been suspected in hypersensitivity reactions to the COVID-19 mRNA vaccines.

The uricase-based treatments for gout provide a good example. The first uricase treatments, derived from non-human hosts, were found to be immunogenic and therefore poorly effective. PEGylation of those uricase enzymes was used to decrease immunogenicity and enhance the pharmacokinetic profile. One example is the marketed uricase product, Pegloticase®. However, clinical studies showed that APAs were induced and detected in more than one third of patients treated with PEGylated uricase for chronic refractory gout, with enhanced enzyme clearance but no anti-uricase antibody detected in any patient. In addition, APA-positive patients treated with PEGylated uricase have experienced cutaneous and infusion-related reactions correlating with higher levels of APAs, as well as loss of urate-lowering efficacy. Similar reactions, such as decreased serum half-life and hepatotoxicity from immune complex formation, have been noted for PEGylated liposomes that are used for delivery of cytotoxic drugs for the treatment of cancer (e.g, LipoDox™). The hypersensitivity and other reactions because of APAs raise concerns regarding the treatment of patients with PEGylated drugs.

The presence of APAs in mammals is therefore not without significant consequences. The present application discloses compounds and methods for preventing the induction of and/or elimination of APAs.

BRIEF DESCRIPTION OF THE INVENTION

The above and other problems associated with APAs have now been solved. The present inventors have found that compounds disclosed herein can treat or prevent the induction of APAs in a PEG-naïve subject as well as suppress APAs and APA generation in subjects experiencing an undesirable anti-PEG immune response.

In one embodiment, a compound is provided, having one of the following formulas:

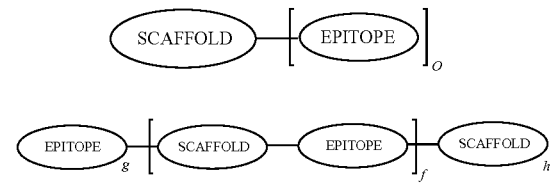

or a pharmacologically acceptable salt thereof;
the scaffolds being the same or different;
the scaffold(s) being covalently bound to the epitope(s);
wherein the epitopes each comprise one or more polyethylene glycol (PEG) groups;
wherein the compound has an effective valency of 2-2;
and wherein:
  is 2-200
  f is 2-200;
  g is 0-1; and
  h is 0-1.

In one embodiment, a method for making the compound is provided, comprising contacting the scaffold with one or more of the epitopes, and covalently bonding the scaffold to one of more of the epitope, to form the compound.

In one embodiment, a compound is provided, having the formula:

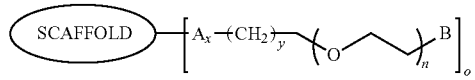

or a pharmacologically acceptable salt thereof;
wherein A is a linking group;
wherein B is an end group;
wherein x is 0 or 1;
wherein y is 0-20;
wherein n>3; and
wherein o is 2-200; and
wherein the compound has an effective valency of 2-12.

In one embodiment, a method for making the compound is provided, comprising contacting a scaffold having the following formula comprising one or more covalent-binding reactive group A' thereon with one or more of an epitope having the following formula comprising a covalent-binding reactive group A" thereon, and covalently bonding, to form the compound; wherein

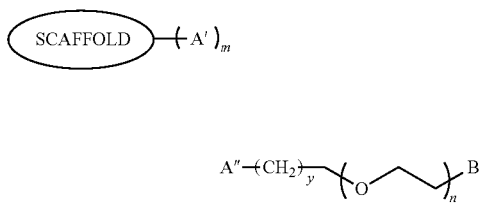

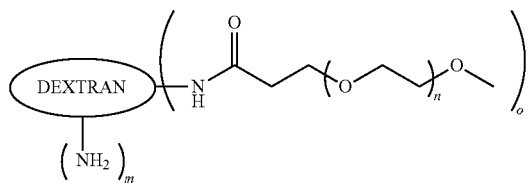

or a pharmacologically acceptable salt thereof;
wherein m is ≥0.
In one embodiment, a compound is provided, having the formula:

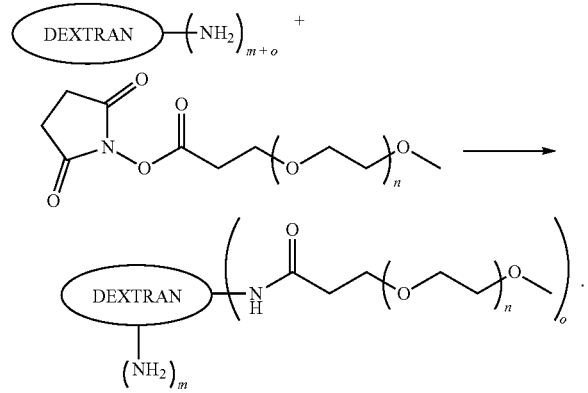

wherein m=0-100;
wherein n≥3;
wherein o is 2-200; and
wherein the compound has an effective valence of 2-12.

In one embodiment, a method for making the compound is provided, comprising carrying out a reaction comprising:

In one embodiment, a composition is provided, comprising the compound and a pharmaceutically acceptable carrier.

In one embodiment, a method is provided for suppressing or preventing an anti-PEG antibody response in a subject in need thereof or at risk thereof, comprising administering to said subject the compound or the composition.

In one embodiment, a method is provided for suppressing or preventing an anti-PEG antibody response in a subject in need thereof or at risk thereof, comprising administering to said subject together or separately the compound or composition, and a PEGylated compound or drug.

In one embodiment, a method is provided for crosslinking a subthreshold number of surface immunoglobulin receptors of a B cell in a subject, which crosslinking does one or more selected from the group consisting of not activate the B cell, inactivate the B cell, destroy the B cell, or a combination thereof, comprising administering to said subject the compound or composition.

In one embodiment, a method is provided for crosslinking a subthreshold number of surface immunoglobulin receptors of a B cell in a subject, which crosslinking does one or more selected from the group consisting of not activate the B cell, inactivate the B cell, destroy the B cell, or a combination thereof, comprising administering to said subject together or separately the compound or composition, and a PEGylated compound or drug.

DETAILED DESCRIPTION OF THE INVENTION

Figure 1:
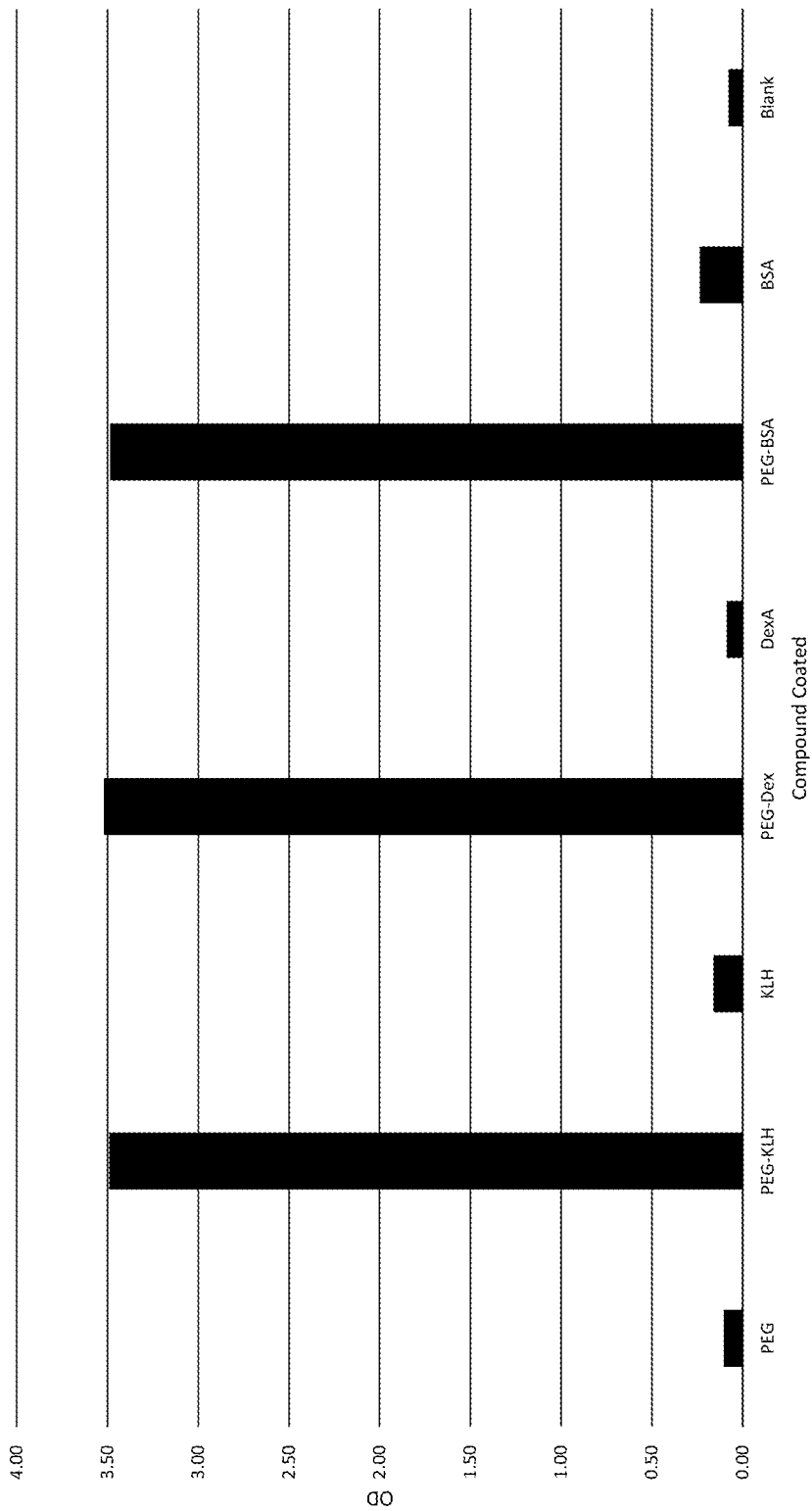
FIG. 1 presents anti-PEG antibody reactivity results observed for comparative and exemplary treatments.

The present inventors have now surprisingly found a successful formula for suppressing APAs.

B-cell activation that results in triggering the cell to proliferate, secrete antibody and switch immunoglobulin production from IgM to other Ig classes (e.g., IgG, IgA, IgE), involves the extensive cross-linking of surface B-cell receptors (BCRs) into a single complex. The cross-linking of BCRs leading to B-cell activation requires a minimum number of BCRs to form a linked complex, i.e., a threshold level of crosslinking needed for antigen immunogenicity and B-cell activation, thus the coining of the term the "immunon" and the "Immunon Hypothesis" (H. M. Dintzis, R. Z. Dintzis, and B. Vogelstein (1976) Molecular determinants of immunogenicity: The immunon model of immune response. Proc. Natl. Acad. Sci. USA 73(10):3671-3675; and R. Z. Dintzis, M. H. Middleton, and H. M. Dintzis, (1985) Inhibition of anti-DNP antibody formation by high doses of DNP-polyacrylamide molecules; effects of hapten density and hapten valence. J. Immunol. 135(1):423-427, incorporated herein by reference in their entireties).

According to the Immunon Hypothesis, B-cell activation by a multi-valent compound (i.e., one having multiple copies of an epitope or hapten on a single molecular structure, each recognized by the BCR) requires the cross-linking of >~10 membrane B-cell receptors into a higher order receptor complex on the surface of the B-cell. Such BCR cross-linking can be achieved through a multi-valent compound with an effective valence of >~10. For a given structure to reach a threshold level of cross-linking that triggers cell activation, i.e., the immunon, a multivalent compound of a minimum length and epitope density is required. Subthreshold arrays (i.e., multivalent compounds that can cross-link receptors but do not reach the immunon threshold) do not activate B-cells but are also not devoid of effects as they can apparently impart a different cell signal that results not in B-cell activation but in cell anergy, tolerance, and/or apoptosis of the cell. As such, although these subthreshold arrays are not activating, they are also not inactive and result in the active suppression of antibody production.

In one embodiment, a 40 kDa PEG chain has an effective valency of 2 to 13. Put another way, a 40 kDa PEG chain has about 2-13 B-cell receptor-accessible PEG epitopes. A single PEG epitope (i.e., receptor binding site) has about 3-10 PEG units. B-cell receptor crosslinking (i.e., to bind more than one B-cell receptor), the next PEG epitope is at least about 100 Å away, or at least about 65-70 PEG units. In one embodiment, ~65-70 PEG units are present between respective B-cell receptor accessible PEG-epitopes, and create the ~100 Å distance between receptor-accessible PEG epitopes, leading to a unit for effective BCR binding on the order of at least 70-80 PEG units. Considering that 40 kDa PEG includes ~900 PEG units, the maximum theoretical effective valence of a 40 kDa PEG is thus ~12 (i.e., 900/80=11.2 or 900/70=12.8), assuming a linear and stretched PEG chain with no tertiary structure. In one embodiment, considering that PEG polymers may have a helical nature in solution, longer PEG polymers are also contemplated. In one embodiment, considering a single BCR can bivalently bind to the same PEG chain, a single BCR could bind to a much longer length of PEG, further increasing the distance between B-cell receptor accessible PEG epitopes to more than the 70-80 PEG units, and these are also contemplated.

In another embodiment, the ~100 Å distance between B-cell receptor accessible PEG epitopes is created by the scaffold. In another embodiment, the 100 Å between B-cell receptor accessible PEG epitopes is created through a combination of intervening PEG units and scaffold.

In another embodiment, the distance between B-cell receptor accessible PEG epitopes is greater than about 100 Å, which includes greater than 100, 110, 150, 200, 300, 400, 500, 600, 1000, 2000, and 3000 Å, or more.

The term "valence" is understood to mean the number of B-cell receptor PEG epitopes on a given molecular structure (i.e., scaffold).

The term "effective valence" is understood to mean the relative capability of a compound (e.g., an immunogen or immunogen preparation) to simultaneously bind a number of receptors on the surface of a target cell, e.g., B-cell receptors on a B-cell, taking into account the epitopes and spacing between them to permit receptor cross-linking. In one embodiment, the effective valence is such that at least some epitopes are spaced at a distance of at least 100 Å or greater apart, in consideration of binding to B-cell receptors. This includes a case wherein a series of epitopes exist, but only the third, or fourth (or tenth, for example) epitope is at least 100 Å apart from another. The 100 Å distance is considered to take into account not the distance through connected atoms and bonds, but instead through space including special and steric hindrance parameters of the compound. In another embodiment, a structure is contemplated with a valence of 50 (i.e., 50 copies of the epitope on a scaffold) but an effective valence of <~10 (i.e., of the 50 copies of the epitope on the polymer, only ~<10 are available for binding to the receptors on a cell).

The term "threshold" is understood to mean that a compound has an effective valence that results in cell activation. In the context of the present invention, the effective valence generally requires an effective valence of >10 (e.g., in the context of the structural and spatial requirements of a B cell receptor, that each of >10 epitopes be spaced at least ~100 Å apart and able to bind cell receptors on surface of a B cell).

The term "sub-threshold" is understood to mean a compound or construct whose effective valency is not sufficient to reach a threshold valency that results in cell activation. In one embodiment, the compound, having at least two epitopes bound to a scaffold, wherein the epitopes bind to B-cell membrane immunoglobulin receptors specific for the epitope but fail to form an immunon.

In one embodiment, the scaffold comprises one or more of polymer, dendrimer, peptide-based dendrimer, poly(propyleneimine) (PPI) dendrimer, peptide dendrimers, glycodendrimer, hybrid dendrimer, poly-L-lysine (PLL) dendrimer, nanoparticle, dextran, cyclodextrin, α-cyclodextrin, β-cyclodextrin, γ-cyclodextrin, dexamine, polyacrylamide, polyvinylpyrolidone, non-ionic synthetic sucrose polymer, carboxymethyl-cellulose, polyvinyl alcohol, poly(D-lysine), poly(D-glutamic acid), D-lysine, poly(L-lysine), poly(L-glutamic acid), L-lysine, human serum albumin, gamma-globulin, liposome, PEG, or combination thereof.

In another embodiment, the scaffold comprises dextran.

In another embodiment, the scaffold comprises a peptide-based dendrimer derived from a D-lysyl-P-alanine (amide) core peptide, subsequent glycine spacer residue addition, and two successive rounds of D-lysine, then glycine addition.

In another embodiment, the scaffold is valence-restricted.

In another embodiment, the scaffold is covalently bound to the epitope or a pharmacologically acceptable salt thereof.

In another embodiment, the compound comprises a PEG, covalently bound via reaction of one or more covalent-binding reactive group on the scaffold with one or more selected from the group consisting of Alkyne PEG, Cleavable PEG, MeNH-PEG, PEG Sulfonic acid, Amino PEG, DBCO PEG, Non-PEG linker, PEG Tosylate, Aminooxy PEG, Diketone PEG, PEG Acid, PEG-X-PEG, BCN-PEG, DNP-PEG, PEG Aldehyde, Poly PEG, Benzyl-PEG, DOTA PEG, PEG Azide, Propargyl PEG, Biotin PEG, DSPE PEG, PEG Maleimide, PROTAC PEG, Bis-PEG-acid, Fluorescent PEG, PEG NHS ester, Sugar PEG, Bis-PEG-NHS, Fmoc PEG, PEG Peptide, TCO-PEG, Boc-PEG, Hydroxy PEG, PEG PFP ester, Tetrazine-PEG, Branched PEG, Lipid PEG, PEG Phosphonate, Thiol PEG, Bromo PEG, m-PEG, PEG Silane, 2-arm activated branched PEG, lysine branched PEG, PEG-NHS, PEG-aldehyde, PEG-maleimide, and a combination thereof.

In another embodiment, the scaffold is non-immunogenic. For example, the scaffold does not induce an immune response by its administration, either alone, or in combination with the epitope.

In another embodiment, the scaffold is soluble in physiologically acceptable aqueous solution, buffer, or both.

In another embodiment, the compound is soluble in physiologically acceptable aqueous solution, buffer, or both.

In another embodiment, o is 10-60, 15-50, or 15-30, or other range, subrange, or value from 2-200 with an effective valence of 2-12. In another embodiment, o is about 20.

In another embodiment, f is 10-60, 15-50, or 15-30, or other range, subrange, or value from 2-200 with an effective valence of 2-12. In another embodiment, f is about 20.

In another embodiment, g is 0 or 1.

In another embodiment, h is 0 or 1.

In another embodiment, the effective valence is about 2-12, which includes 2, 3, 4, 5, 6, 7, 8, 9, 10, 11 and 12 and all values and subranges therebetween.

In another embodiment, wherein y is 0-20, which includes 0, 1, 2, 3, 4, 5, 6, 7, 8, 9, 10, 12, 14, 16, 18 and 20, which includes all values and subranges therebetween.

In another embodiment, the epitope comprises a polymer having —(OCH$_2$CH$_2$)$_{3-300}$—, —(OCH$_2$CH$_2$)$_{3-100}$, —(OCH$_2$CH$_2$)$_{3-50}$—, —(OCH$_2$CH$_2$)$_{3-50}$—, —(OCH$_2$CH$_2$)$_{4-30}$—, —(OCH$_2$CH$_2$)$_{26}$—, —(OCH$_2$CH$_2$)$_{23}$—, —(OCH$_2$CH$_2$)$_{22}$—, —(OCH$_2$CH$_2$)$_{21}$—, —(OCH$_2$CH$_2$)$_{20}$—, —(OCH$_2$CH$_2$)$_{6}$—, or other range, subrange or value of —(OCH$_2$CH$_2$)— groups.

In another aspect, a method is provided for making the compound, comprising contacting the scaffold with one or more of the epitope, and covalently bonding the scaffold to one of more of the epitope, to form the compound.

In another embodiment, A is a linking group formed from a reaction of a covalent-binding reactive group on the scaffold with one or more selected from the group consisting of Alkyne PEG, Cleavable PEG, MeNH-PEG, PEG Sulfonic acid, Amino PEG, DBCO PEG, Non-PEG linker, PEG Tosylate, Aminooxy PEG, Diketone PEG, PEG Acid, PEG-X-PEG, BCN-PEG, DNP-PEG, PEG Aldehyde, Poly PEG, Benzyl-PEG, DOTA PEG, PEG Azide, Propargyl PEG, Biotin PEG, DSPE PEG, PEG Maleimide, PROTAC PEG, Bis-PEG-acid, Fluorescent PEG, PEG NHS ester, Sugar PEG, Bis-PEG-NHS, Fmoc PEG, PEG Peptide, TCO-PEG, Boc-PEG, Hydroxy PEG, PEG PFP ester, Tetrazine-PEG, Branched PEG, Lipid PEG, PEG Phosphonate, Thiol PEG, Bromo PEG, m-PEG, PEG Silane, 2-atm activated branched PEG, lysine branched PEG, PEG-NHS, PEG-aldehyde, PEG-maleimide, and a combination thereof.

The Alkyne PEG, Cleavable PEG, MeNH-PEG, PEG Sulfonic acid, Amino PEG, DBCO PEG, Non-PEG linker, PEG Tosylate, Aminooxy PEG, Diketone PEG, PEG Acid, PEG-X-PEG, BCN-PEG, DNP-PEG, PEG Aldehyde, Poly PEG, Benzyl-PEG, DOTA PEG, PEG Azide, Propargyl PEG, Biotin PEG, DSPE PEG, PEG Maleimide, PROTAC PEG, Bis-PEG-acid, Fluorescent PEG, PEG NHS ester, Sugar PEG, Bis-PEG-NHS, Fmoc PEG, PEG Peptide, TCO-PEG, Boc-PEG, Hydroxy PEG, PEG PFP ester, Tetrazine-PEG, Branched PEG, Lipid PEG, PEG Phosphonate, Thiol PEG, Bromo PEG, m-PEG, PEG Silane referred to herein are available from BroadPharm, San Diego, CA and NOF America, White Plains, NY, are disclosed as functionalized PEGs at their websites, https://broadpharm.com. Other suitable PEG compounds are available from NOF America Corporation of White Plains, NY, US. https://www.nofamerica.com.

In another embodiment, when x is 0, then A is a covalent bond.

In another embodiment, A is a group having the formula, —NHCO—, —CONH—, —NH—, —CO—, —O—, —COO—, —C(O)(CH$_2$)$_3$C(O)N(H)—, —OCH$_2$C(O)NH(CH$_2$)$_p$NH—, where p is 2-8, —OOC—, —S—, —SH—, —NCH$_2$—, —CH$_2$N—, =N—, —N=, -nucleophile-, or

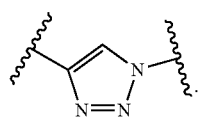 [SMILES: *c1cn(*)nn1]

Other examples of suitable linking groups are disclosed in U.S. Pat. No. 5,599,912, issued Feb. 4, 1997, incorporated herein by reference in its entirety.

In another embodiment, B is a group having the formula, —OH, —OCH$_3$, —OCH$_2$CH$_3$, —OCH$_2$CH$_2$CH$_3$, —CH$_3$, —C$_2$H$_5$, —C$_3$H$_7$, —C$_4$H$_9$, —C$_5$H$_{11}$, —COOH, —COO—, —COOCH$_3$, —COOCH$_2$CH$_3$, —COOC(CH$_3$)$_3$, —NH(CO)CH$_2$NH(CO)OC(CH$_3$)$_3$, —NH(CO)OC(CH$_3$)$_3$, —NH(CO)CH$_2$NH$_2$, COOC(CH$_3$)$_3$, COOC(CH$_3$)$_3$, —N$_3$, —NH$_2$, —NH$_3$$^+$.

In another aspect, a method is provided for making the compound, comprising contacting a scaffold having the following formula comprising one or more covalent-binding reactive group A' thereon with one or more of an epitope having the following formula comprising a covalent-binding reactive group A" thereon, and covalently bonding, to form the compound;

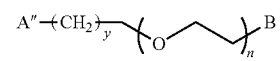

or a pharmacologically acceptable salt thereof;
wherein m is ≥0.

In another embodiment, A' and A" react to form a linking group A, or a covalent bond.

In another aspect, a compound is provided, having the formula:

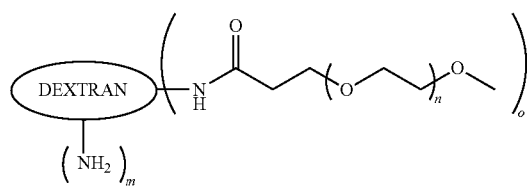

wherein m=0-100;
wherein n>3;
wherein o is 2-70.

In another embodiment, the dextran has a molecular weight (MW) of about 10-80 kDa, about 35-45 kDa, or about 40 kDa, other range, subrange, or value.

In another embodiment, the dextran has a molecular weight (MW), in which >95% is within the range of about 10-80 kDa, about 35-45 kDa, or about 40 kDa. In another embodiment, dextran has a molecular weight (MW) in which >95% is within the range of about 35-45 kDa.

In another embodiment, m=0. That is, all of the —NH$_2$ groups on the dextran react with the corresponding reactive group on the PEG portion.

In another embodiment, o=20.

In another embodiment, n=4 to 300, 4 to 50, 4 to 30, 4 to 26, 23, other range, subrange or value.

In another aspect, a compound is provided, produced by a process comprising:

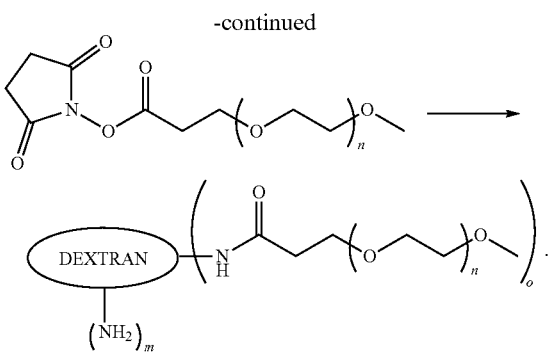

In another aspect, a method is provided for making the compound, comprising carrying out a reaction comprising:

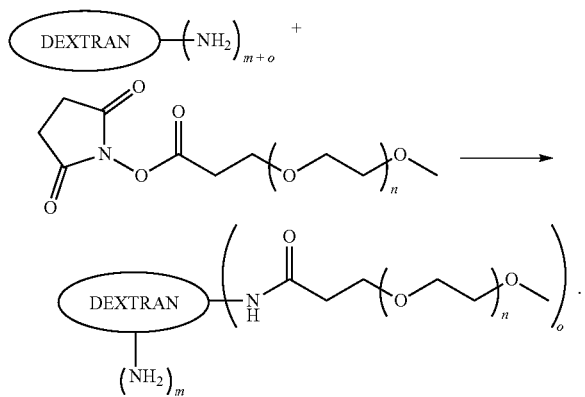

In another embodiment, the compound is a subthreshold construct compound, for crosslinking a subthreshold number of surface immunoglobulin receptors of a B cell, which crosslinking does one or more selected from the group consisting of not activate the B cell, inactivate the B cell, destroy the B cell, or a combination thereof.

In another aspect, a composition is provided, comprising the compound and a pharmaceutically acceptable carrier.

In another embodiment, the composition comprises a PEGylated compound or drug.

In another embodiment, the composition further comprises an immunogenic, antigenic, or reactogenic PEGylated compound or drug. These terms are generally understood by one of ordinary skill in the art to which this application pertains. For example, an immunogenic compound or drug is considered to induce an immune response by its administration: an antigenic compound or drug is considered to reacts with an existing antibody; and a reactogenic compound or drug is considered to provoke an adverse side effect mediated via immune response interaction with its administration.

As used herein the term "immunogenicity" refers to the induction of an immune response by an injected preparation of PEG-modified or unmodified compound or drug (the antigen, e.g., uricase, PEG-uricase; lipid, PEG-lipid), while "antigenicity" refers to the reaction of an antigen with preexisting antibodies. Collectively, antigenicity and immunogenicity are referred to as "immunoreactivity." In previous studies of PEGylated compounds or drugs, immunoreactivity is assessed by a variety of methods, including: 1) the reaction in vitro of PEGylated compound or drug with preformed antibodies; 2) measurements of induced antibody production; and 3) accelerated clearance rates of PEGylated compound or drug after repeated injections.

The present compound is effective to suppress APAs in a subject. The APAs are not particularly limited, and may be induced through either T-independent or T-dependent pathways. Examples of T-independent antigens are PEGylated lipids and/or PEGylated liposomes; and an example of a T-dependent antigen is a PEGylated protein. In one embodiment, the APAs are induced via a T-dependent antigen.

As used herein the term "infusion reaction" is an undesired and unintended effect of a PEGylated compound or drug typically occurring immediately or within 2-48 hours after the PEGylated compound or drug or placebo infusion that cannot be reasonably attributed to another cause. In particular, an adverse drug reaction occurs at doses used for prophylaxis, diagnosis or therapy.

Reactogenicity refers to a subset of reactions that occur soon after vaccination or compound or drug treatment, and are a physical manifestation of the inflammatory response to vaccination or compound or drug exposure. In clinical trials, information on expected signs and symptoms after vaccination or compound or drug exposure is actively sought (or 'solicited'). These symptoms may include pain, redness, swelling or induration for injected vaccines, and systemic symptoms, such as fever, myalgia, headache, or rash. The broader term 'safety' profile refers to all adverse events (AEs) that could potentially be caused/triggered or worsened at any time after vaccination, and includes AEs, such as anaphylactic reactions, diseases diagnosed after vaccination or compound or drug exposure and autoimmune events.

In another embodiment, the composition further comprises a PEGylated compound or drug, wherein the PEGylated compound or drug is one or more of PEGylated antibody, PEGylated enzyme, PEGylated structural protein, PEGylated substrate protein, PEGylated hormone, PEGylated hormone variant, PEGylated hormone biosimilar, PEGylated cytokine, PEGylated lipid, PEGylated liposome, PEGylated synthetic peptide, PEGylated nucleic acid, or a combination thereof.

In another embodiment, non-limiting examples of the composition further comprises a PEGylated compound or drug, wherein the PEGylated compound or drug is one or more of Certolizumab, Phenylalanine ammonia-lyase, Asparaginase, Adenosine deminase, Uricase, Antihemophilic Factor VIII and variants, Factor IX, Insulin, Erythropoietin, G-CSF, Growth hormone, Growth hormone variant, Interferon beta-1a, Interferon alpha-2a, Interferon alpha 2b, irinotecan hydrochloride trihydrate-liposome, doxorubicin-liposome, Sulfur hexafluoride-lipid contrast agent, Octafluoropropane-lipid contrast agent, Naloxol, Erythropoiesis-stimulating agent (ESA), Aptamer, Universal red blood cells, Nucleic Acid (DNA or RNA), or a combination thereof.

In another embodiment, non-limiting examples of the composition further comprises a PEGylated compound or drug, wherein the PEGylated compound or drug is one or more of Cimzia™ (certolimuzmab pegol), Palynziq™ (Pegvaliase), L-asparaginase, Oncaspar™ (Pegaspargase), Asparlas™ (Calaspargase pegol; PEG-asparaginase), Adagen™ (pegademase bovine), Revcovi™ (Elapegademase), Krystexxa™ (Pegloticase), Adynovate™/Adynovi™ (Rurioctocog alfa pegol, peg-factor VIII), Jivi™ (Damactocog alpha pegol, peg-factor VIII), Esperoct (peg-factor VIII), Turoctocog alpha pegol (peg-factor VIII), Rebinyn™/Relixia™ (Nonacog beta pegol, glycoPEGylated factor IX), Plegridy™ (peginterferon beta-1a), Peglispro™ (peg-human insulin analog), Mircera™ (mPEG-EPO beta), Neulasta™/Fulphila™/Lapelga™/Pelgraz™/Pelmeg™/Ziextenzo™/Neulapeg™ (pegfilgrastim, peg-granulocyte colony-stimulating factor), Lonquex™ (lipegfilgrastin), Somavert™ (pegvisomant, human growth hormone, human growth hormone mutein antagonist), Jintrolong™ (peg-human growth hormone), Besremi™ (Ropeginterferon alpha-2b), Pegasys™ (peginterferon alpha 2b), Pegiutron™/Sylatron™ (interferon-α2b), Omontys™ (Peginasatide); Onivyde™ (irinotecan in PEGylated liposome), Pegbelfermin™ (BMS-986036, PEG-Fibroblast growth factor 21 analogue) Doxil™/Caelyx™ (Doxorubicin HCl in PEGylated liposomes), Jivi™ (PEGylated recombinant antihemophilic factor), Macugen™ (Pegaptanib), Sonovue, Lumason™ (sulfur hexafluoride lipid-type A microspheres), Definity™/Luminitym (Perflutren lipid microspheres), Movantik™/Moventig™ (Naloxegol), Macugen™ (Pegaptanib, Pegnivacogin, synthetic peptide with erythropoietic functions), Comarnaty™ (tozinameran, COVID-19 mRNA vaccine containing peg-lipid); mRNA-1273 (COVIC-19 mRNA vaccine containing peg-lipid). or a combination thereof.

In another embodiment, the composition further comprises a PEGylated compound or drug, wherein the PEGylated compound or drug is a PEGylated uricase.

In another embodiment, the composition further comprises a PEGylated compound or drug, wherein the PEGylated compound or drug is Pegloticase®.

In another aspect, a method of suppressing or preventing an anti-PEG antibody response in a subject in need thereof or at risk thereof is provided, comprising administering to said subject the compound of any claim herein or the composition.

In one embodiment, the subject is a mammal. In one embodiment, the subject is a human. In another embodiment, the antibody response is an IgG or IgM antibody response.

In another aspect, a method of suppressing or preventing an anti-PEG antibody response in a subject in need thereof or at risk thereof is provided, comprising administering to said subject together or separately the suppressive compound or composition, and a PEGylated compound or drug.

In another embodiment, the PEGylated compound or drug is an immunogenic, antigenic, or reactogenic PEGylated compound or drug.

In another aspect, a method is provided for crosslinking a subthreshold number of surface immunoglobulin receptors of a B cell in a subject, which crosslinking does one or more selected from the group consisting of not activate the B cell, inactivate the B cell, destroy the B cell, or a combination thereof, comprising administering to said subject the compound or the composition.

In another aspect, a method is provided for crosslinking a subthreshold number of surface immunoglobulin receptors of a B cell in a subject, which crosslinking does one or more selected from the group consisting of not activate the B cell, inactivate the B cell, destroy the B cell, or a combination thereof, comprising administering to said subject together or separately the compound or composition, and a PEGylated compound or drug.

In one embodiment, the scaffold may be dendrimer, nanoparticle, or the like.

Non-limiting examples of dendrimers include G1, G2, G3, G4 dendrimers, Poly(propyleneimine) (PPI) dendrimers, Peptide dendrimers, Glycodendrimers, Hybrid dendrimers, Poly-L-lysine (PLL) dendrimers, and the like.

For example, generation G4 dendrimer with 64 amino groups at the periphery starts from an ethylene diamine core; the branches or arms were attached by exhaustive Michael addition to methyl acrylate followed by exhaustive aminolysis of the resulting methyl ester using ethylene diamine, as is known. Other dendrimers may be found in Elham Abbasi et al Dendrimers: synthesis, applications, and properties Nanoscale Res Lett. 2014; 9(1): 247. PMID: 24994950; Tomalia D A, Baker H, Dewald J, Hall M, Kallos G, Martin S, Roeck J, Ryder J, Smith P: Dendritic macromolecules: synthesis of starburst dendrimers. Macromolecules 1986, 19:2466-2468; Wang, J., Yang, H. Superelastic and pH-Responsive Degradable Dendrimer Cryogels Prepared by Cryo-aza-Michael Addition Reaction. Sci Rep 8, 7155 (2018). https://doi.org/10.1038/s41598-018-25456-y; Matsuoka, K., Albrecht, K., Yamamoto, K. et al. Mulifunctional Dendritic Emitter: Aggregation-Induced Emission Enhanced, Thermally Activated Delayed Fluorescent Material for Solution-Processed Multilayered Organic Light-Emitting Diodes. Sci Rep 7, 41780 (2017). https://doi.org/10.1038/srep41780; and Ana Santos, et al Dendrimers as Pharmaceutical Excipients: Synthesis, Properties, Toxicity and Biomedical Applications Materials 2020, 13, 65; doi:10.3390/ma13010065. Other dendrimers include those made by cascade synthesis of polyaza compounds, in which a cascade reaction sequences developed for the synthesis of 'non-skid-chain like' polyazamacrocyclic compounds are provided (Buhleier E, Wehner W, Vogtle F: "Cascade"- and "nonskid-chain-like" synthesis of molecular cavity topologies. Synthesis 1978, 1978(2):155-158).

Non-limiting examples of some nanoparticles may be found in Szymanski P, Markowicz M, Mikiciuk-Olasik E: Nanotechnology in pharmaceutical and biomedical applications: Dendrimers. Nano Brief Rep Rev 2011, 6:509-539; Rukmani Thiruppathi et al Nanoparticle Functionalization and Its Potentials for Molecular ImagingAdv. Sci. 2017, 4, 1600279; Gang Bao et al Multifunctional Nanoparticles for Drug Delivery and Molecular imaging, Annu Rev Biomed Eng. 2013; 15: 253-282. doi:10.1146/annurev-bioeng-071812-152409; and Kim Sapsford et al Functionalizing Nanoparticles with Biological Molecules: Developing Chemistries that Facilitate Nanotechnology Chem. Rev. 2013, 113, 3, 1904-2074.

Scaffolds made from different polymeric support shapes are also contemplated. Non-limiting examples may be found in Lu, Y., Nemoto, T., Tosaka, M. et al. Synthesis of structurally controlled hyperbranched polymers using a monomer having hierarchical reactivity. Nat Commun. 8, 1863 (2017). https://doi.org/10.1038/s41467-017-01838-0.

EXAMPLES

Experimental Procedure PEG-BSA & PEG-Dextran

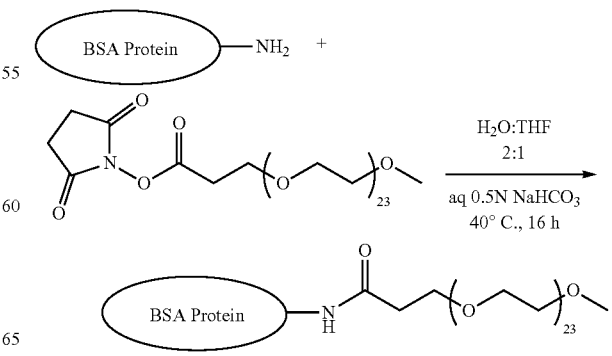

To a solution of BSA protein (40 mg) in 3 mL of 33% THF in H₂O and 0.5 mL of 0.5N aq NaHCO₃ was added PEG-24-NHS (40 mg; Broad Pharma, Cat. #BP-22247). Then the reaction mixture was allowed to mix in an incubator over night at 40° C. The solvent was evaporated under reduce pressure at 40° C., and dried under high vacuum and washed with ethyl acetate afford the PEG-BSA conjugated product.

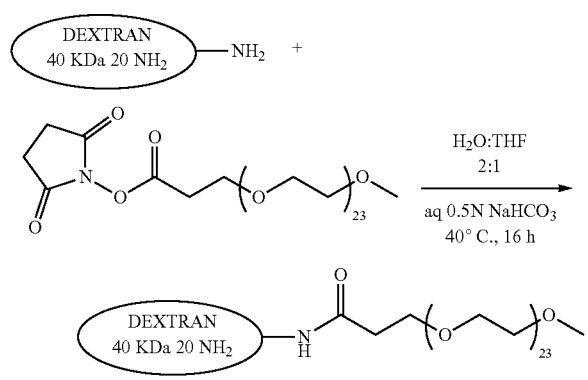

To a suspension of Dextran (30 mg; Amino-Dextran, 40 kDa dextran functionalized with 20 amino groups; FinaBio Cat. #AD40x20) in 3 mL of 33% THF in H₂O and 0.5 mL of 0.5N aq NaHCO₃ was added PEG-24-NHS (30 mg; Broad Pharma, Cat. #BP-22247) at 0° C. The mixture was then allowed to mix in an incubator over night at 40° C. The solvent was then evaporated under reduce pressure at 40° C., dried under high vacuum, and washed with ethyl acetate to afford the PEG-Dextran conjugated product.

Experimental Procedure for Reporter Linker

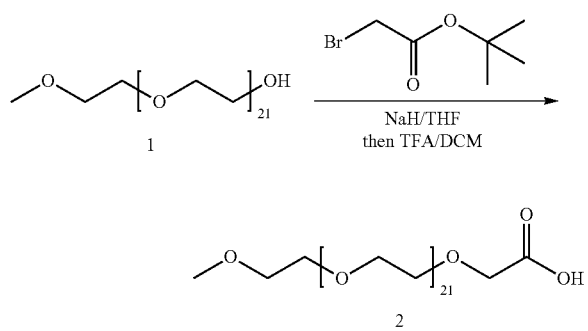

Poly(ethylene glycol) methyl ether (1) (mPEG; 1.0 gm; 0.99 mmol) was dissolved in THF and cooled to 0° C. then NaH (60% in oil; 79.2 mg; 1.98 mmol; 2.0 equiv) was added and the mixture was stirred for 10 minutes. Then tert-butyl 2-bromoacetate (231.7 mg; 1.19 mmol; 1.2 equiv) was added to the reaction mixture with stirring, and the mixture was warmed to 50° C. overnight with stirring. MeOH was added and the solvent was removed in vacuo. The product was dissolved in CHCl₃ and filtered on celite then purified through a silica gel pad.

The resulting ester was dissolved in 1.5 mL of formic acid and stirred at room temperature for 3 h. The solvent was removed in vacuo and the residue was co-evaporated with CHCl₃ (3×3 mL) to yield the desired carboxylic acid (2).

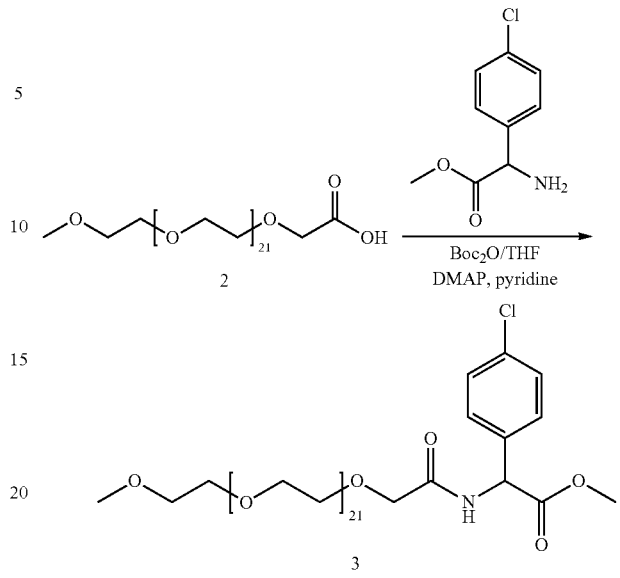

(Monomethoxy)polyethylene glycol acetic acid (2; 1.0 gm; 0.94 mmol)) was dissolved in anhydrous DCM, then cooled to 0° C. Pyridine (96.6 mg; 1.2 equiv), and DMAP (cat. amount) was added to the reaction mixture followed by di-tert-butyl dicarbonate (Boc-anhydride; 212.57 mg; 1.22 equiv) and the reaction was stirred for 10 min at 0° C. Then methyl 4-chloro-phenyl glycine (187.65 mg; 1.0 equiv) was added to the reaction mixture. The mixture was warmed to room temperature and stirred overnight. The solvent was evaporated under vacuum. The residue was dissolved in 5 mL of DCM, and the crude product was precipitated with ethyl ether (30 mL) to provide the amide 3.

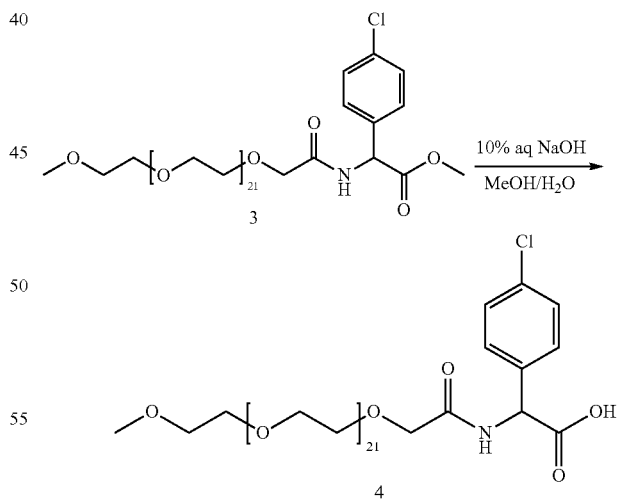

Compound 3 was dissolved in 50% MeOH water (2 mL), then excess 10% NaOH (0.5 mL) was added to the mixture and it was stirred at room temperature overnight. MeOH (2 mL) was added, and the mixture was neutralized with 10% aq HCl at 0° C. The solvent was removed in vacuo. The product was dissolved in CHCl₃ and filtered on celite then purified through a silica gel pad to give carboxylic acid 4.

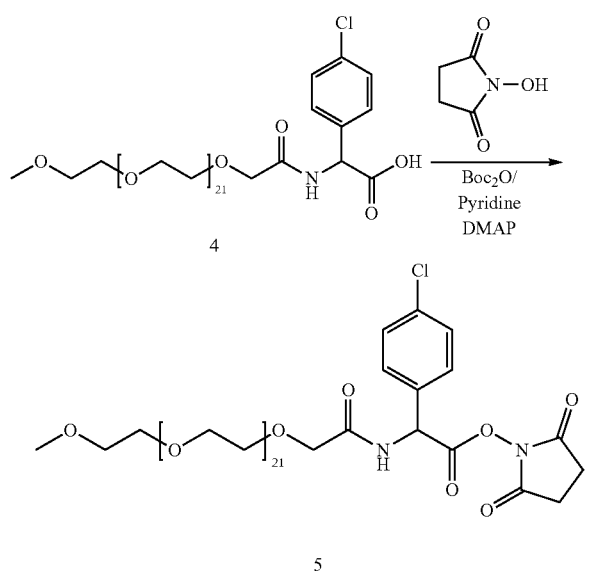

Carboxylic acid 4 (1.0 gm; 0.81 mmol) was dissolved in anhydrous THF (3 mL), then pyridine (83.8 mg; 1.05 mmol; 1.3 equiv), DMAP (cat amount), and di-tert-butyl-di-carbonate (Boc-anhydride; 169.36 mg; 0.97 mmol; 1.2 equiv) was added to the reaction mixture at 0° C. and stirred for 10 min. Then N-hydroxy succinate (93.22 mg; 0.81 mmol; 1.0 equiv) was added to the reaction mixture and the mixture was stirred at room temp for 2 hours. The solvent was removed in vacuo. The product was dissolved in $CHCl_3$ and filtered on celite then purified through a silica gel pad to give the NHS-ester 5.

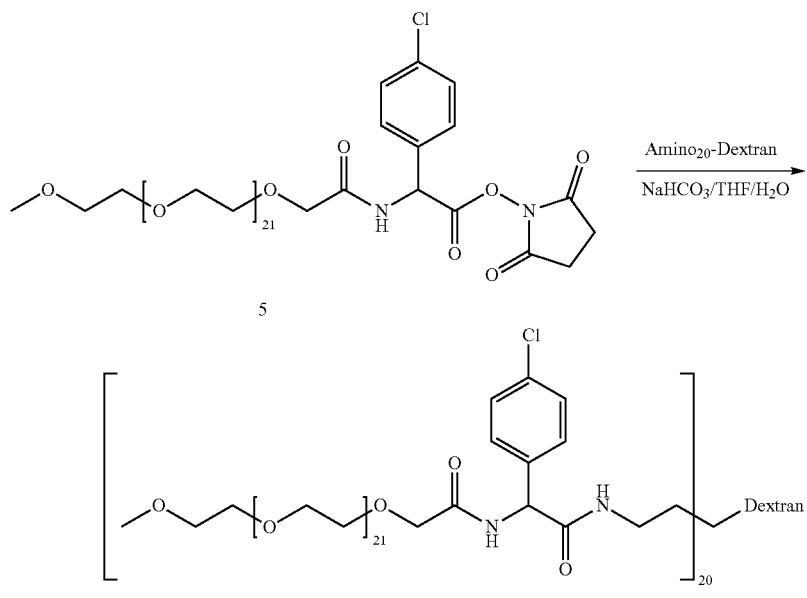

To a solution of Amino Dextran (1.0 g; 0.5 mmol amine) in 3 mL (33% THF in $H_2O$) and $NaHCO_3$ (210.0 mg; 2.5 mmol; 5.0 equiv) at 0° C., was added NHS ester 5 (860 mg; 0.65 mmol; 1.3 equiv) and the mixture was stirred overnight at 40° C. The solvent evaporated under reduce pressure and the product was dried under high vacuum, to provide a powder/residue. This material was then washed with ethyl acetate, with vigorous mixing. The solid was allowed to settle and the ethyl acetate was decanted. This washing step was repeated 10 times. The solid material was dried under high vacuum to afford the product 6 which was used without further purification.

The purpose of the reporter linker is for ease of characterization of the conjugate produced. The chlorophenyl glycine represents one mole of PEG attached to the amino dextran. In this way, NMR or chlorine elemental analysis may be used to quantify the loading of the PEG to the Dex, which will significantly aid in manufacturing the conjugate. The aromatic signals in the NMR spectra will not overlap with the dextran or PEG signals which will make it easier to interpret.

Confirmation of PEG Conjugations

ELISA was used for confirmation of PEG conjugation to various scaffolds. ELISAs were carried out as follows. Plates were coated overnight at 4° C. with 0.5 mcg various antigens (e.g., BSA, PEG-BSA, as noted below) in 100 uL sodium carbonate coating buffer, then washed twice with Phosphate Buffered Saline (PBS) and blocked with 300 uL Blocking Buffer (nonfat dry milk-PBS (5% w/v) or 1× fish gel (Rockland Immunochemicals)) at room temperature for 1 hr. Anti-PEG antibody (GenScript THE™ PEG Antibody, mouse monoclonal, Cat. No. A01795) diluted in Blocking Buffer and 100 uL per well incubated for 1 hr at room temperature. Wells were then washed 3× for 5 min each with PBS, and secondary antibody reagent (anti-mouse IgM-HRP or anti-mouse IgG-HRP, as appropriate; 100 uL) incubated for 1 hr at room temperature. After washing 3× for 5 minutes each with PBS, 100 uL chromogenic substrate (3,3',5,5'-Tetramethylbenzidine, TMB) for ELISA (TMBE) peroxidase reactions was added to each well and a kinetic read taken for 5 minutes. Plates were allowed to continue the color development reaction for a total of 30 minutes at which time 100 uL stop solution was added and plates read.

As shown in FIG. 1, anti-PEG antibody reactivity was observed only when conjugated to large scaffolds such as Keyhole Limpet Hemocyanin (KLH), amino-dextran (DexA), or Bovine Serum Albumin (BSA). This confirmed that these scaffolds were appropriately PEGylated.

Anti-PEG Animal Model

Male BALB/c mice (aged 6-8 weeks) were immunized intraperitoneally (i.p.) with PEG conjugated to KLH (PEG-KLH) using Complete Freund's adjuvant on Day 1 (50 mcg) and boosted with the same conjugate using Incomplete Freund's adjuvant on Day 18 (25 mcg). Pre-immunization blood samples were collected by retroorbital bleeding on Day −5. All other blood draws were collected on the days indicated. For testing, pools of serum from each group (n=5) were generated by mixing equal volumes of serum from each mouse in the group. Treatments were as outlined below.

ELISAs were carried out as follows. Plates were coated overnight at 4° C. with 0.5 mcg antigen in 100 uL sodium carbonate coating buffer, then washed twice with PBS and blocked with 300 uL Blocking Buffer (nonfat dry milk-PBS (5% w/v) or 1× fish gel (Rockland immunochemicals)) at room temperature for 1 hr. Antibodies and sera were then diluted (1:500) in Blocking Buffer as indicated, and 100 uL per well incubated for 1 hr at room temperature. Wells were then washed 3× for 5 min each with PBS, and secondary antibody reagent (100 uL) incubated for 1 hr at room temperature. After washing 3× for 5 minutes each with PBS, 100 uL TMBE was added to each well and a kinetic read taken for 5 minutes. Plates were allowed to continue the color development reaction for a total of 30 minutes at which time 100 uL stop solution was added and plates read.

Treatments consisted of i.p. injection of the following:
PEG-Dex conjugate: PEG-Dextran conjugate, 500 mcg in 250 uL PBS
PEG (free PEG): MeO-23PEG-Ethanolamine (PEG-24-NHS treated with ethanol amine to form an amide bond that mimics the linkage to the scaffolds, Dex, KLH, or BSA), 187.5 mcg in 250 uL PBS (PEG molar equivalent to that used in the Dex-PEG group)
DexA+PEG: Mixture of 312.5 mcg amino-dextran mixed with 187.5 mcg MeO-23PEG-Ethanolamine (free PEG) in 250 uL PBS (PEG molar equivalent to that used in the PEG-Dex group)

Figure 2:
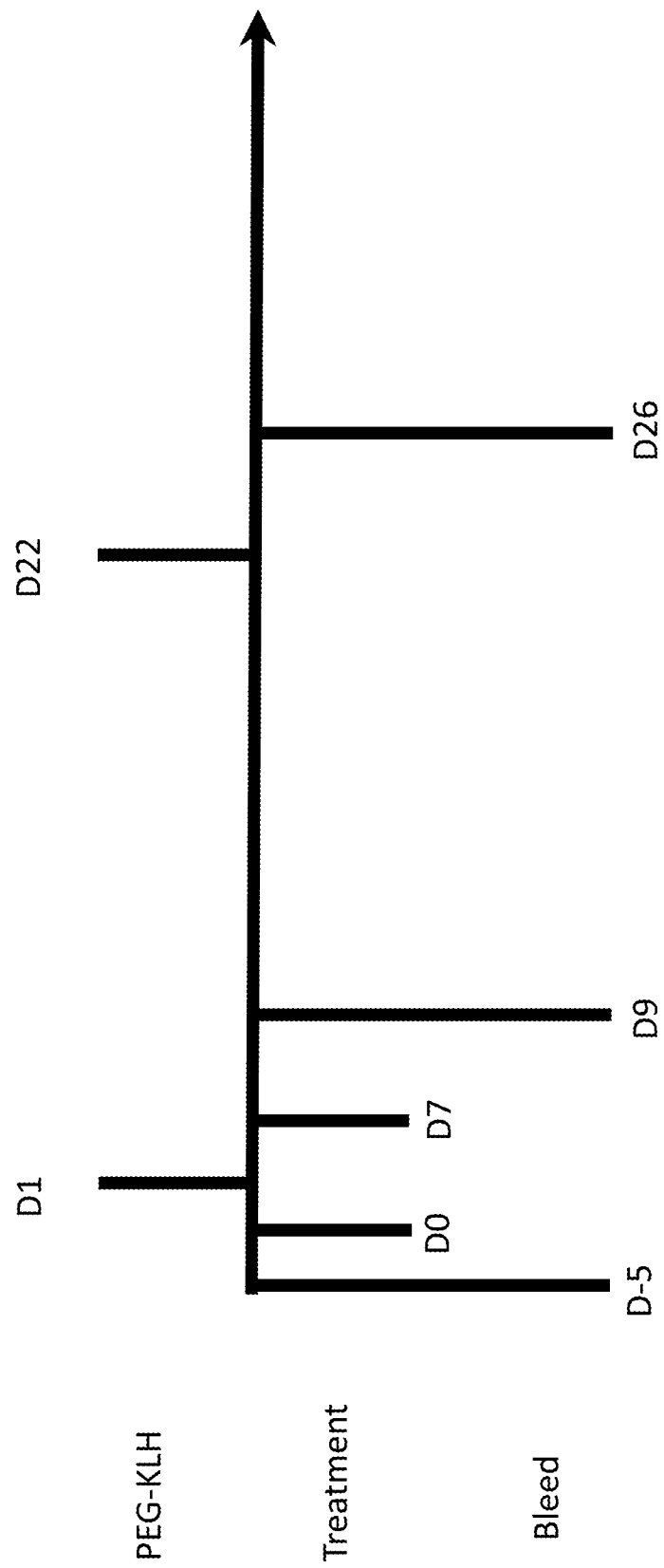
FIG. 2 shows a timeline for anti-PEG IgM antibody response experiment.

In the present experiment, we first studied the anti-PEG IgM antibody response. We modeled a clinical setting in which a PEG-naïve patient (i.e., no existing anti-PEG antibody response) begins treatment with a PEGylated therapeutic drug (e.g., a PEGylated biologic), i.e., "prophylaxis" model. The mice were immunized with the immunogenic PEG-KLH conjugate (Day 1) to generate an anti-PEG antibody response, with PEG-Dex, PEG or DexA+PEG treatments (as noted above) administered on Day 0 and Day 7. Anti-PEG IgM antibodies were then measured against PEG-BSA by ELISA from bleeds collected on Day −5 and Day 9 (serum dilution 1:500)(FIG. 2).

Figure 3:
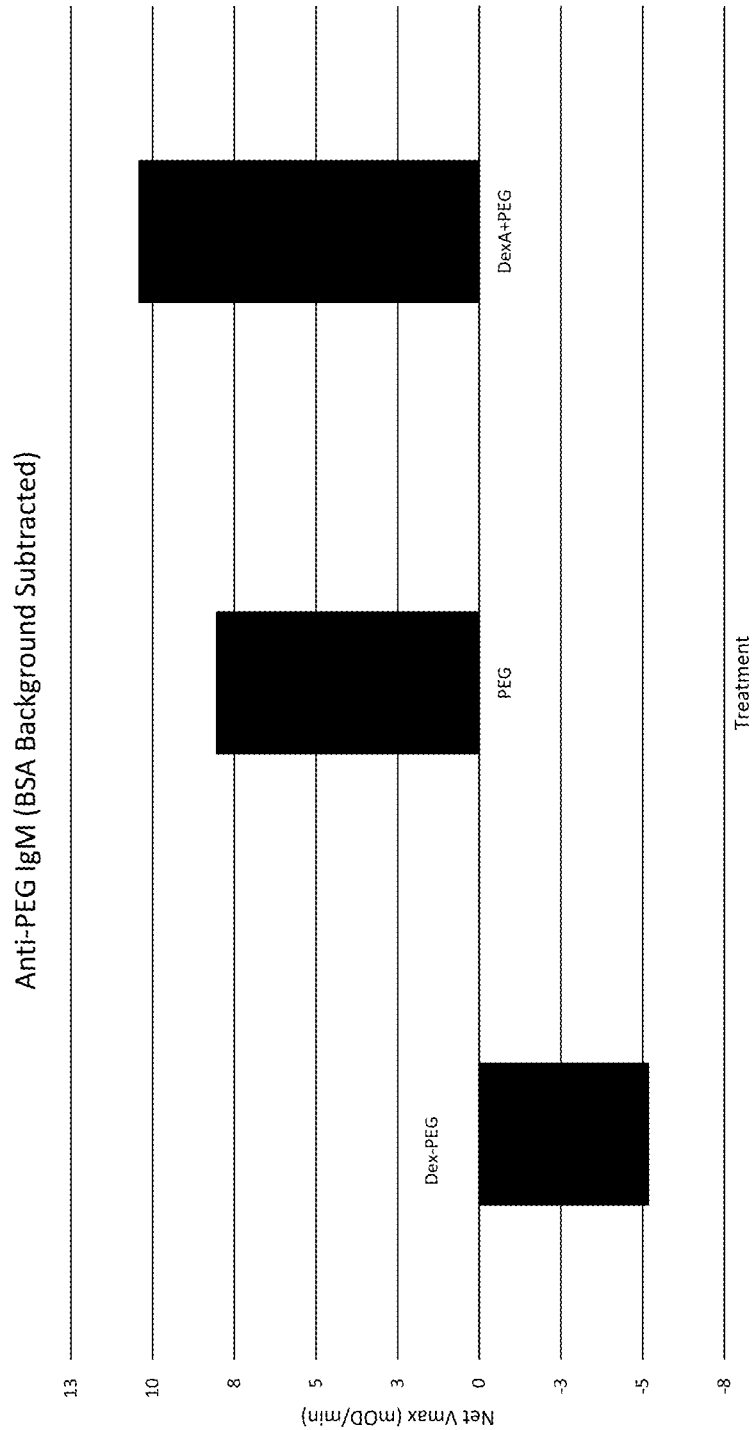
FIG. 3 presents anti-PEG IgM results observed for comparative and exemplary treatments.

No anti-PEG IgM antibodies were detected in the pre-bleed (Day −5) samples (data not shown). As shown in FIG. 3 by Day 9, anti-PEG IgM antibodies were readily detected in the groups treated with free PEG (i.e., molar equivalent to that used in the PEG-Dex group), or treatment with a mixture of DexA+PEG (i.e., molar equivalents to that used in the PEG-Dex group, mixed and not conjugated). In contrast, the group treated with the PEG-Dex conjugate resulted in no detectable anti-PEG IgM antibody response. Suppression of anti-PEG IgM antibody is thus achieved and demonstrated to require conjugation of the PEG moiety to the dextran suppressive scaffold (PEG-Dex).

In the present experiment, detection of IgG antibodies on Day 9 is not generally expected as this antibody subclass generally takes two weeks or more to emerge after immunization. We therefore followed the IgG immune response in these same animals by providing an additional PEG-KLH immunization on Day 22 and measured anti-PEG IgG antibodies using bleeds collected on Day 26. The anti-PEG IgG response was assessed by ELISA as described above, using a serum dilution of 1:500.

Figure 4:
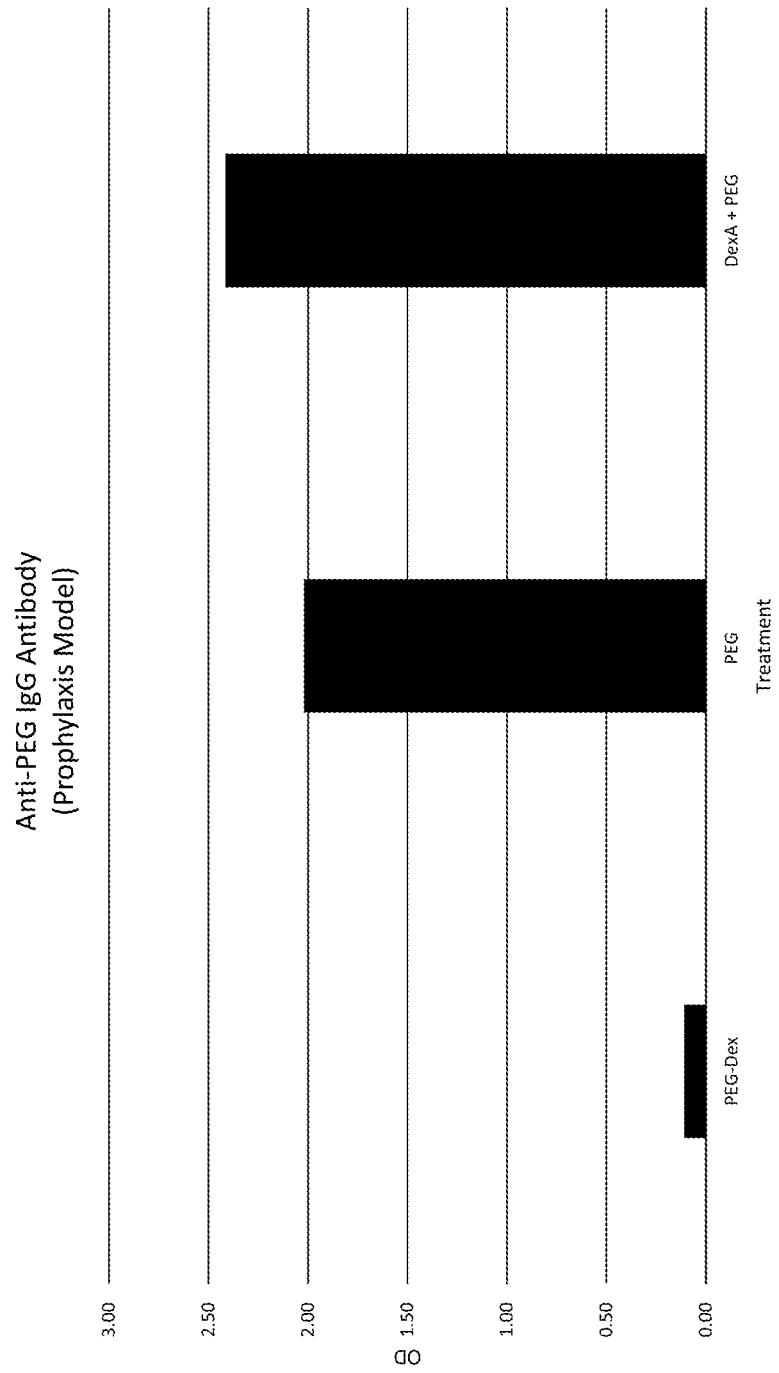
FIG. 4 presents anti-PEG IgG antibody results observed for comparative and exemplary treatments.

As shown in FIG. 4, treatment with the suppressive PEG-Dex conjugate, administered weeks earlier, resulted in a lack of an anti-PEG IgG antibody response even after boosting with the immunogenic PEG-KLH conjugate in Freund's adjuvant. IgG antibodies to the KLH protein carrier were observed in all three groups after booster as expected (data not shown). In contrast, anti-PEG IgG antibodies were readily detected only in the PEG (free PEG) and DexA+PEG (mixed and unconjugated components) groups, but not in the PEG-Dex conjugated group. The anti-PEG IgG antibody suppression was thus observed only in the PEG-Dex conjugate group, a result of treatment starting prior to the first PEG-KLH immunization, and thus an effect that was observed for at least two weeks from last treatment, and also in spite of immunogenic boosting. This effect on anti-PEG antibody suppression was specific to PEG as observed by a lack of suppression of the antibody response to the KLH protein carrier (data not shown). These data thus indicate that prophylaxis against development of an anti-PEG antibody response can be achieved in a subject.

Another bleed sample collected on Day 67 showed relative anti-PEG antibody levels to those above (data not shown), indicating that even five weeks after the PEG-KLH boost on Day 22, the prophylactic treatment on Day 0 and Day 7 with PEG-Dex conjugate still suppressed anti-PEG antibody production in vivo. To explore effects on the treatment groups that did not suppress anti-PEG antibody responses (i.e., PEG and DexA+PEG), all animals were given an additional administration of PEG-Dex on Day 70, followed by another boost with PEG-KLH on Day 71. Bleeds collected on Day 73 and Day 80 showed no detectable anti-PEG antibody was present, indicating that the existing anti-PEG antibody responses observed in the animals on Day 67 could be reduced (data not shown).

Figure 5:
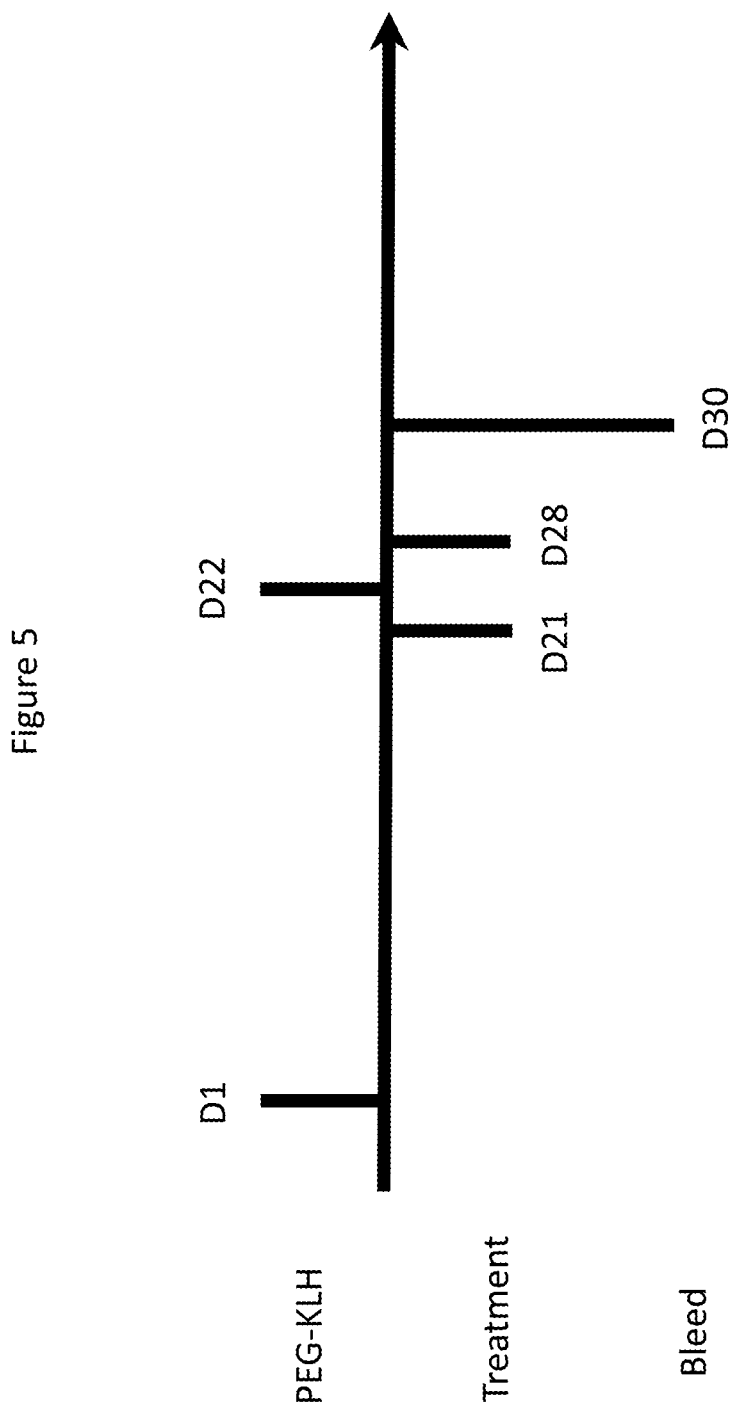
FIG. 5 shows a timeline for an experimental treatment.

We next wanted to explore the clinical setting whereby the subject to be treated with a PEGylated therapeutic drug had an existing anti-PEG antibody response, i.e., a "treatment" model. In this treatment scenario, to generate anti-PEG antibodies prior to treatment, mice were first immunized with PEG-KLH conjugate on Day 0 and boosted on Day 22 (FIG. 5). This immunization strategy generated high levels of anti-PEG antibodies. Treatments with PEG-Dex, PEG or DexA+PEG (as noted above) were administered on Day 21 and Day 28 as indicated. Anti-PEG IgG antibodies were measured on Day 30 by ELISA as indicated above (serum diluted 1:500). In this treatment model, there is an existing and robust anti-PEG IgG antibody response at the time treatments are administered, which is in contrast to the prophylaxis model of treatment illustrated in the previous example above where no anti-PEG IgG antibody is present at the time of treatment.

Figure 6:
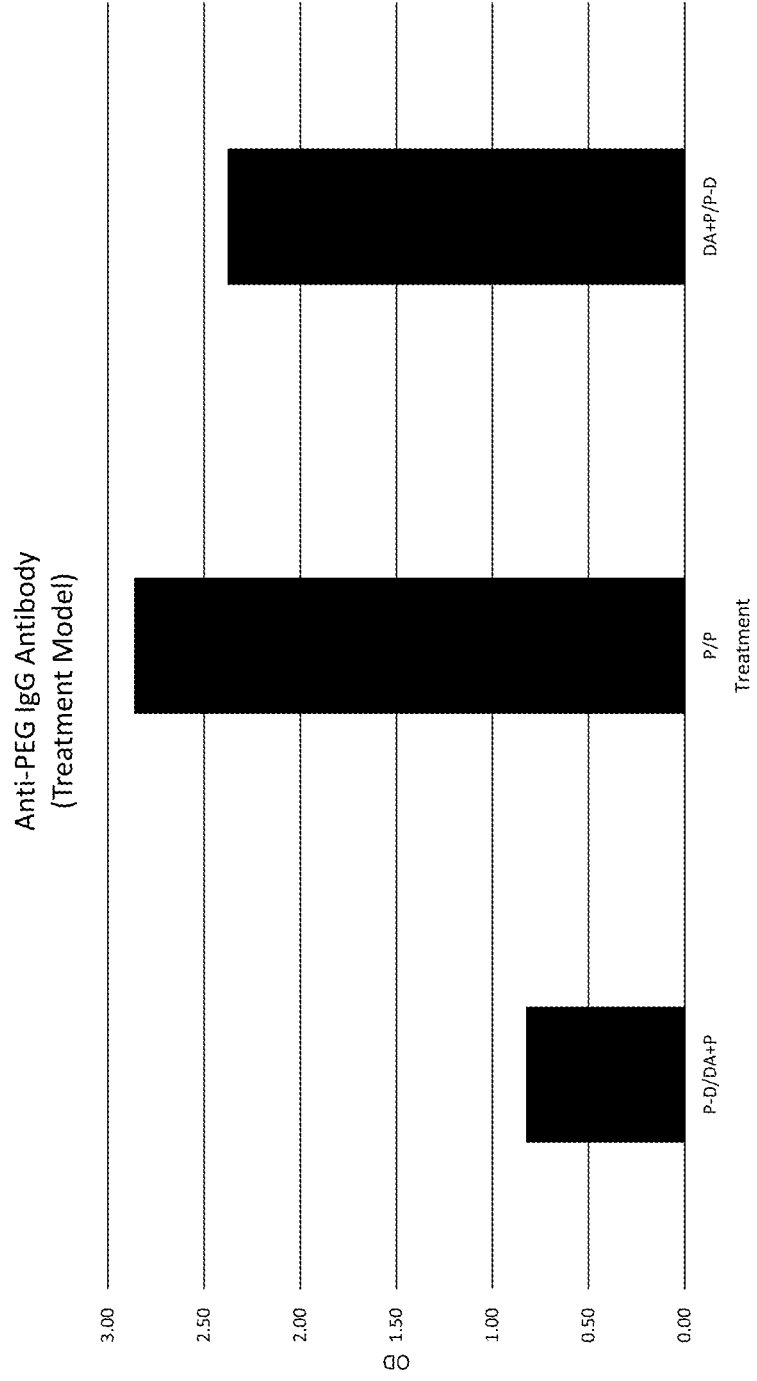
FIG. 6 presents anti-PEG IgG antibody results observed for comparative and exemplary treatments.

In this experiment, we wished to explore the kinetics of the suppressive response in the face of an existing and boosted anti-PEG IgG antibody environment. Two treatments were administered, one before and one after the PEG-KLH immunogenic boost. Treatments were the non-suppressive free PEG alone (P) or the DexA+PEG mixture (P+D), or the suppressive PEG-Dex conjugate (P-D). As shown in FIG. 6, administration of PEG alone, before and after PEG-KLH boosting (P/P), had no effect on anti-PEG IgG antibodies. This is in agreement with the prophylaxis experiment described above where PEG alone did not suppress anti-PEG antibody responses. However, treatment of animals with the PEG-Dex conjugate did suppress anti-PEG IgG antibody responses. For example, administration of the PEG-Dex conjugate two days after boosting with PEG-KLH, when a strong IgG antibody booster response would be underway, resulted in a decrease in anti-PEG IgG antibody response within two days of treatment (DA+P/P-D). Interestingly, and in contrast to the treatments with molar equivalents of PEG alone or the DexA+PEG mixture, administration of the PEG-Dex conjugate the day before PEG-KLH boosting resulted in a greatly diminished anti-PEG IgG antibody response by 4 days after the boost (P-D/DA+P). Higher and/or more frequent doses are therefore expected to more rapidly lower the existing anti-PEG antibody response. As with the previous experiments, no suppression of anti-KLH IgG antibodies was observed due to suppression of anti-PEG IgG antibody (data not shown).

Another bleed sample collected on Day 67 showed persistence of the relative anti-PEG antibody levels to those from the Day 30 bleeds, but an additional administration of PEG-Dex on Day 70, followed by another boost with PEG-KLH resulted in no detectable anti-PEG antibody on Day 73 and Day 80 (data not shown). This indicated that existing anti-PEG antibody responses can be eliminated in animals previously exposed to PEG and generating antibody to PEG.

Figure 7:
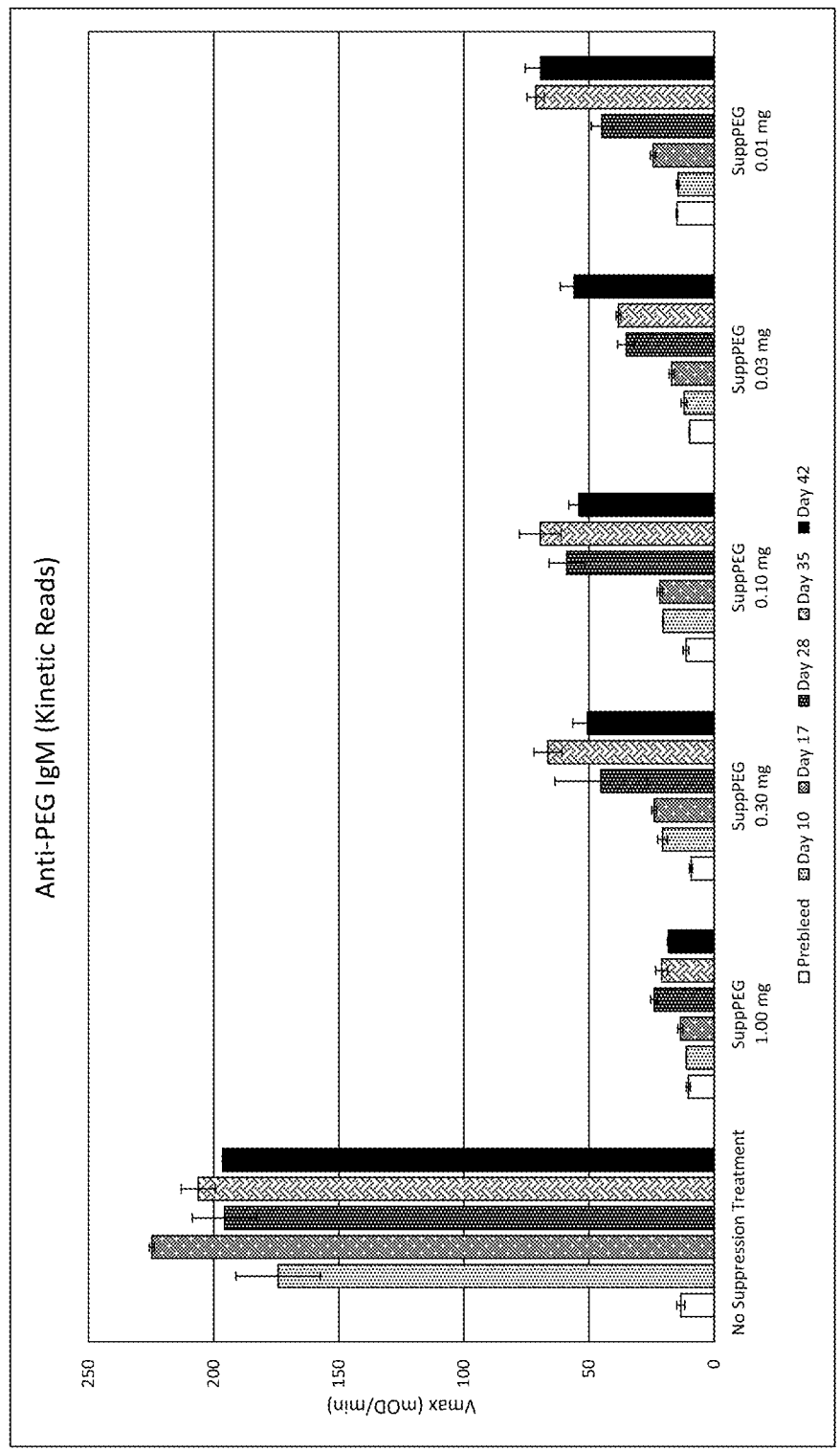
FIG. 7 presents results observed for anti-PEG antibody suppressive effects of different doses of PEG-Dex in a PEG-naïve animal model.

In a separate experiment, we assessed the anti-PEG antibody suppressive effects of different doses of PEG-Dex in the PEG-naïve animal model. This model is analogous to a patient without existing anti-PEG antibodies initiating therapy with a PEGylated drug. In this dosing study, animals were treated just once with various closes of PEG-Dex on Day 0. All animals were then immunized (50 mcg PEG-KLH in CFA) and boosted (25 mcg PEG-KLH in IFA) on Days 1 and 22. Serum samples from all animals were obtained on Days −5, 10, 17, 28, 35, and 42. All serum samples were tested as pools composed of equal volumes of serum from individual mice in each group. As shown in FIG. 7, a single dose of PEG-Dex as low as 10 mcg/mouse was able to completely suppress production of anti-PEG IgM antibody titers (i.e., signal same as No Suppression Treatment control group). Upon boosting on Day 22 with the PEG-KLH immunogen, some IgM was detected in the lower dose groups but IgM production was still greatly inhibited until at least Day 42.

Figure 8:
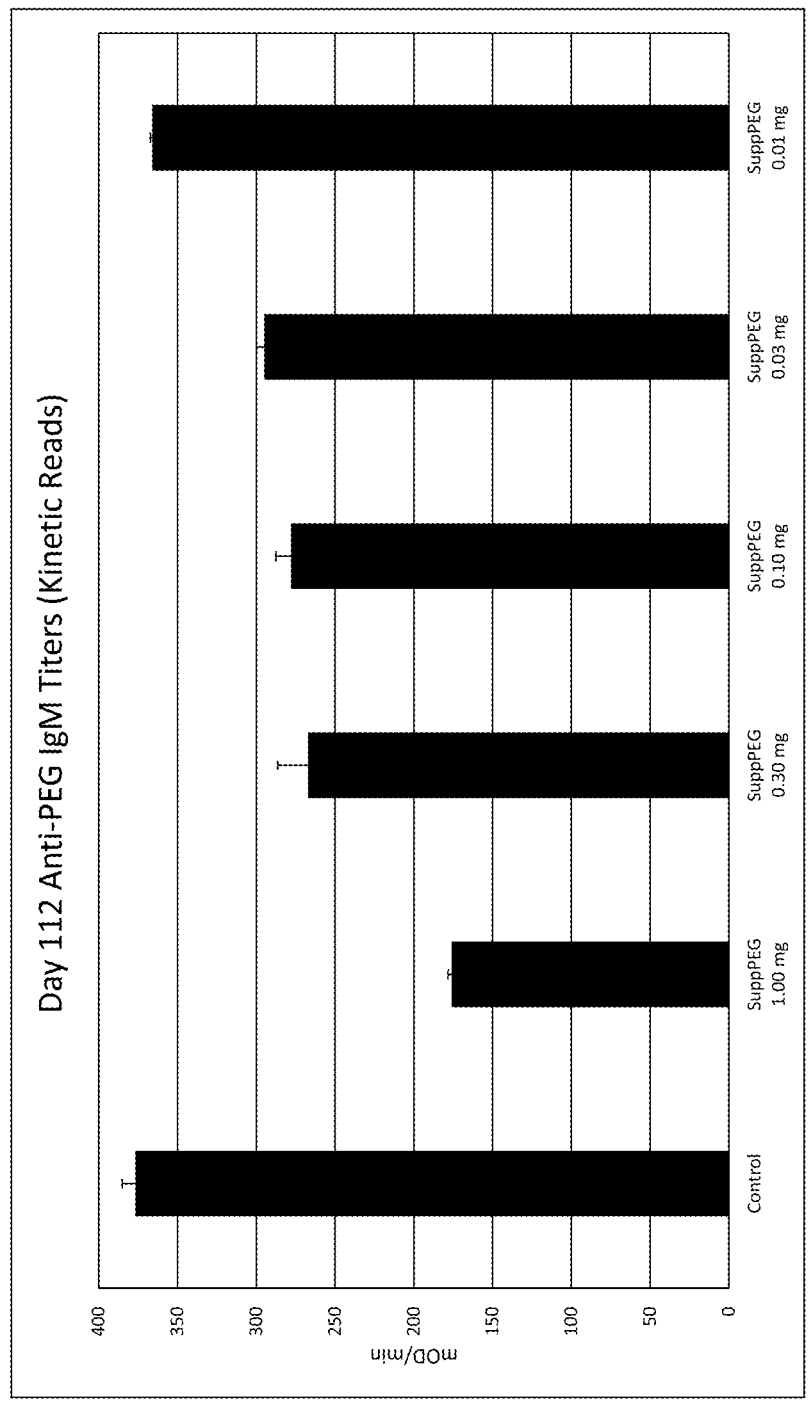
FIG. 8 presents results observed after PEG-KLH boosting on day 98.

After a long rest period, the animals were again boosted with PEG-KLH immunogen on Day 98 and bleeds collected on Day 112. At almost 4 months after the single PEG-Dex dose administered on Day 0, the lowest dose of 10 mcg per mouse did not suppress production of anti-PEG IgM antibody from the boost at Day 98 (FIG. 8). The higher PEG-Dex doses (0.03-0.3 mcg), however, did suppress anti-PEG antibody production to about 75% of the No Treatment control, and the highest dose tested (1 mg) suppressed more than 50% (FIG. 8). By this measure, a single dose of 1 mg PEG-Dex almost 4 months prior was able to suppress anti-PEG IgM production even with repeated and strong immunostimulation with PEG-KLH immunogen.

Figure 9:
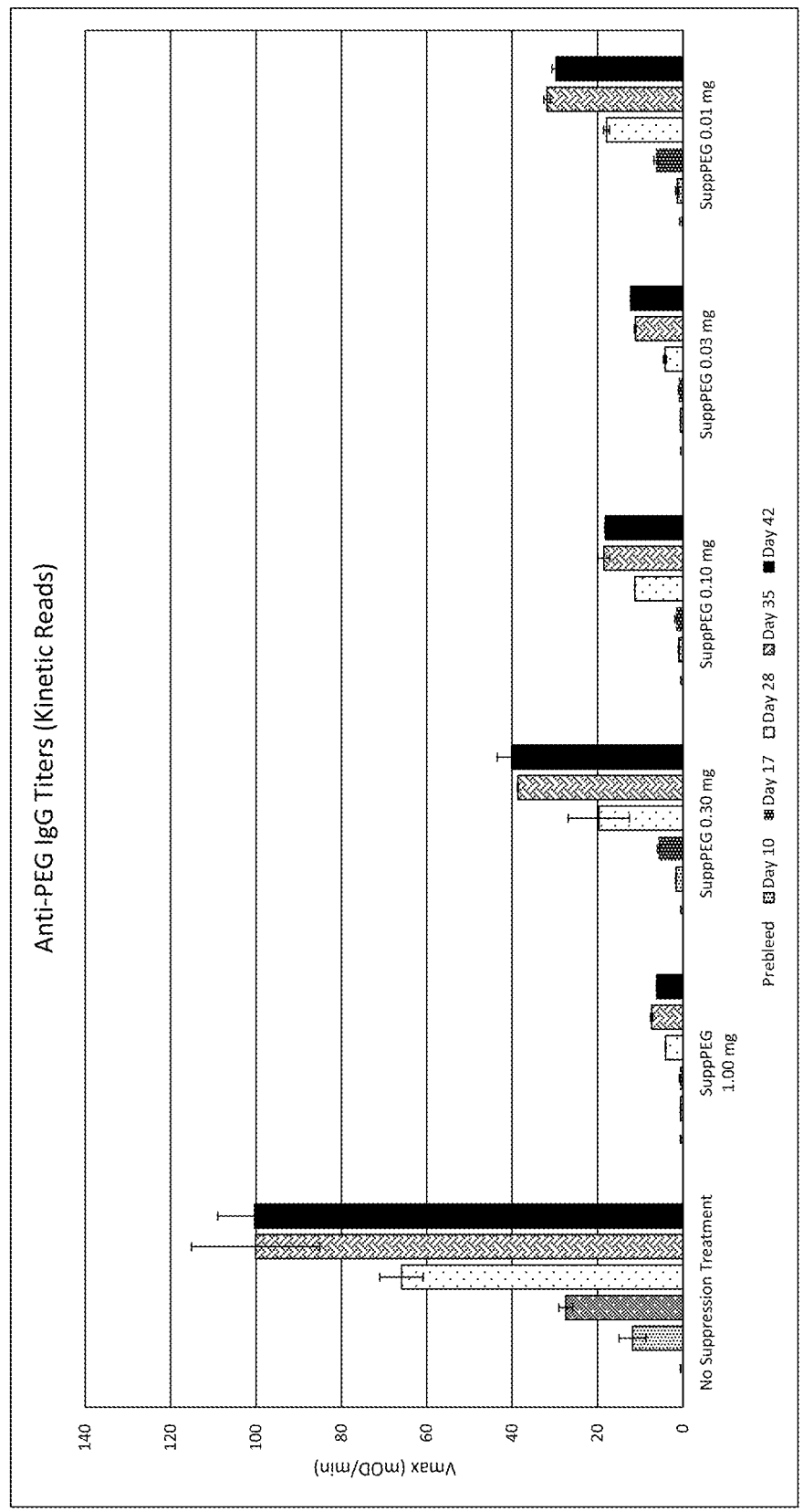
FIG. 9 presents results observed for exemplary and comparative treatments.

In comparison to the IgM response, analysis of the IgG responses showed a delay of anti-PEG IgG antibody generation in the No Treatment group as expected (in contrast to IgM production that peaks on Day 7-10, IgG production lags by at least a week)(FIG. 9). Similar suppression by the PEG-Dex conjugate was also observed as previously reported. The highest dose (1 mg) resulted in less than 5% the antibody level as the No Treatment control, with the lower doses resulting in 10-25% the levels of IgG as measured in our assays.

Figure 10:
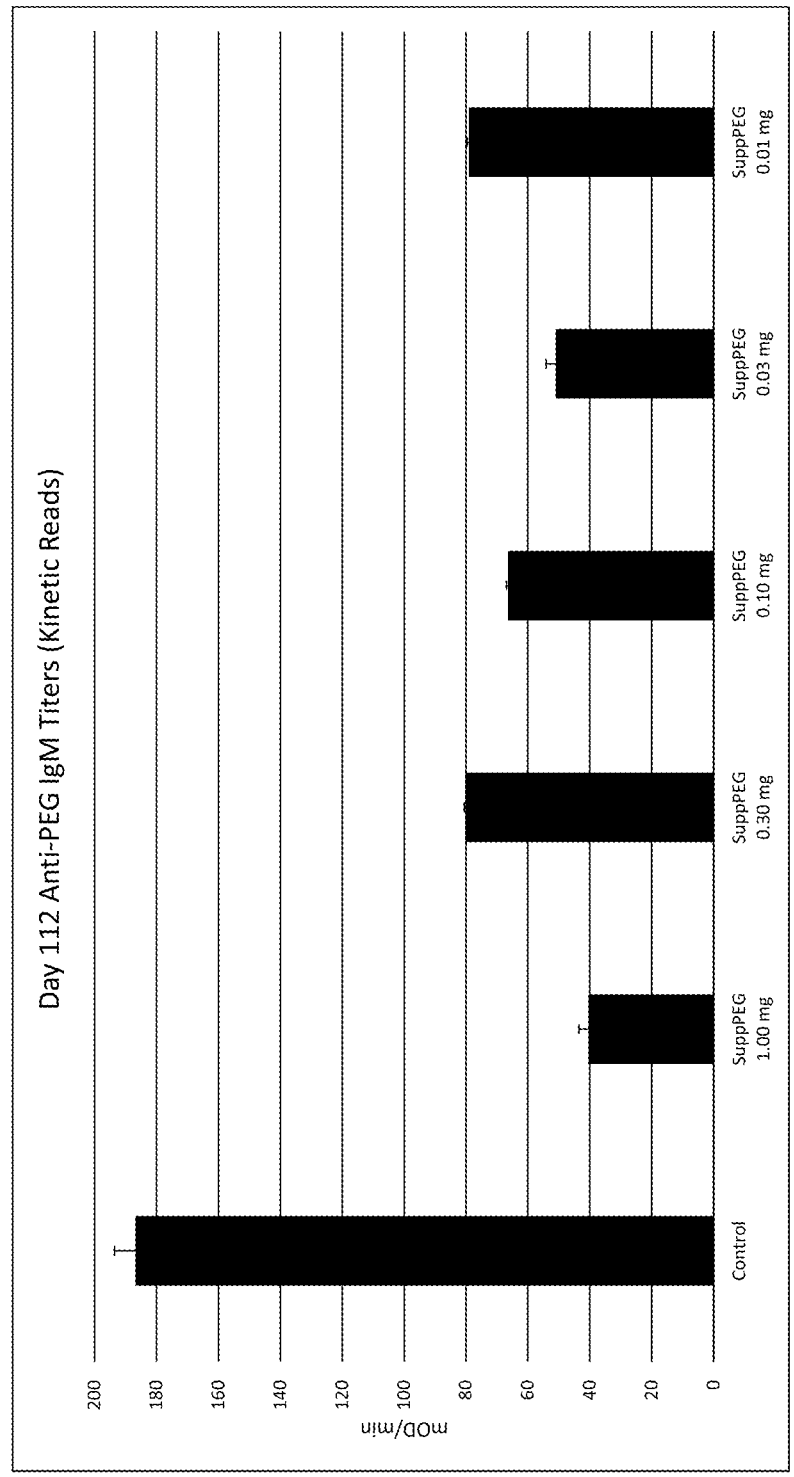
FIG. 10 presents results observed for exemplary and control treatments.

After boosting with PEG-KLH immunogen on Day 98, the levels of anti-PEG IgG antibody in the 1 mg suppression group were only 20% of the No Treatment control group (FIG. 10). Even the lower doses, including the 10 mcg/mouse group, were able to suppress anti-PEG antibody levels to ~42% of levels observed in the control group. Strong suppression of anti-PEG IgG antibody was thus observed from treatment almost 4 months earlier with 1 mg PEG-Dex. A single dose of 1 mg PEG-Dex was therefore able to suppress anti-PEG IgM and IgM production even with repeated and strong immunostimulation with PEG-KLH immunogen.

Figure 11:
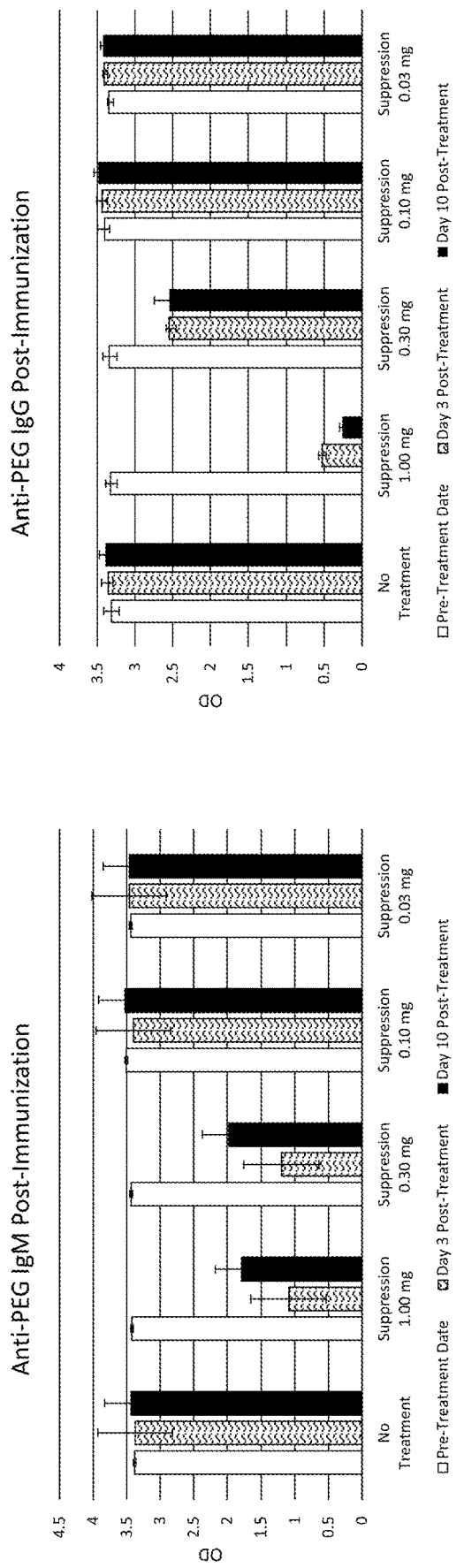

We then explored dosing with PEG-Dex in a PEG-exposed animal model. This is analogous to a patient with an existing anti-PEG antibody level initiating therapy with a PEGylated drug. In this dosing study, animals were first immunized (50 mcg PEG-KLH in CFA, Day 1) and boosted (25 mcg PEG-KLH in IFA, Day 22) with PEG-KLH to generate a high anti-PEG antibody titers. Animals were then treated just once with various doses of PEG-Dex on Day 34. Serum samples from all animals were obtained after the PEG-KLH boost but prior to treatment with PEG-Dex (Day 30), with additional bleeds taken three and 10 post-treatment with PEG-Dex (Days 37 & 44, respectively). All serum samples were tested as pools composed of equal volumes of serum from individual mice in each group. As shown in FIG. 11, in this PEG-exposed model with high levels of anti-PEG antibodies, the single lowest doses of PEG-Dex (0.03 and 0.10 mg) were not able to completely eliminate anti-PEG IgM or IgG antibody. In contrast, treatment with 1.00 mg PEG-Dex did significantly suppress both anti-PEG IgM and IgG antibody titers. An intermediate PEG-Dex dose (0.30 mg) suppressed IgM, and partially suppressed IgG. A single dose of 1 mg PEG-Dex was thus able to suppress anti-PEG IgM and IgG levels in animals with high anti-PEG antibody levels resulting from previous exposure to a PEGylated agent. These data suggest that higher treatment doses may be needed for suppression of anti-PEG antibodies in subjects with high existing levels of anti-PEG antibodies compared to antibody-naïve subjects.

Figure 12:
FIG. 12 presents results observed for comparative and exemplary treatments.

In an additional experiment, we explored ability of PEG itself to suppress anti-PEG antibody responses. In this experiment, animals were treated just once with PEG-Dex (mPEG-Dex), mPEG-10 (10 kDa PEG), or mPEG-40 (40 kDa PEG) on Day 0. Compound doses were adjusted to contain equivalent mass of mPEG (100 mcg). All animals were immunized then immunized (50 mcg mPEG-KLH in CFA) Day 1 and boosted on Day 30 (25 mcg mPEG-KLH in IFA). Serum samples from all animals were obtained on Days −5 (PB), 10, 19, and 35. All serum samples were tested as pools (1:500 dilution) composed of equal volumes of senior from individual mice in each group. As shown in FIG. 12, and as previously demonstrated, a single dose of mPEG-Dex was able to completely suppress production of anti-mPEG IgM and IgG antibody production. In contrast, the mPEG-10 and mPEG-40 preparations were not able to suppress production of anti-PEG NM antibody. Furthermore, the mPEG-10 preparation was not able to suppress production of anti-PEG IgG antibody, and the mPEG-40 preparation partially suppressed anti-PEG IgG production prior to the mPEG-KLH boost, but not afterwards as high levels of anti-PEG IgG antibodies were induced after boosting. The PEG-Dex construct was clearly superior to the free PEG preparations and able to totally inhibit production of anti-PEG antibodies whether the immune stimulation was via a T-independent antigen (e.g., PEGylated lipids or PEGylated liposomes) or a T-dependent antigen (e.g., a PEGylated protein).

The relevant contents of each reference, patent, and patent publication cited herein are hereby incorporated, the same as if set forth at length.

The invention claimed is:

1. A compound, having the formula:

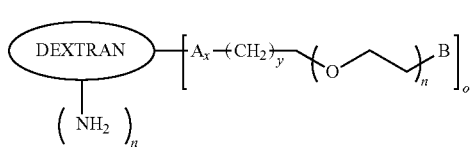

or a pharmacologically acceptable salt thereof;
wherein:
A is a linking group having the formula —NHCO—, —CONH—, —NH—, —CO—, —O—, —COO—, —C(O)(CH$_2$)$_3$C(O)N(H)—, —OCH$_2$C(O)NH(CH$_2$)$_p$NH— where p is 2-8, —OOC—, —S—, —SH—, —NCH$_2$—, —CH$_2$N—, =N—, —N=, or

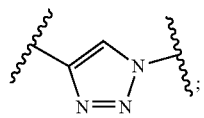 [SMILES: *c1cn(*)nn1]

B is an end group having the formula -OH, —OCH$_3$, —OCH$_2$CH$_3$, —OCH$_2$CH$_2$CH$_3$, —CH$_3$, —C$_2$H$_5$, —C$_3$H$_7$, —C$_4$H$_9$, —C$_5$H$_{11}$, —COOH, —COO, —COOCH$_3$, —COOCH$_2$CH$_3$, —COOC(CH$_3$)$_3$, —NH(CO)CH$_2$NH(CO)OC(CH$_3$)$_3$, —NH(CO)OC(CH$_3$)$_3$, —NH(CO)CH$_2$NH$_2$, COOC(CH$_3$)$_3$, COOC(CH$_3$)$_3$, —N$_3$, —NH$_2$, or —NH$_3^+$;
m is 0 to 100;
x is 0 or 1;
y is 0 to 20;
n is 4 to 50;
o is 2 to 200; and
wherein the dextran has a molecular weight (MW) of about 40 kDa, in which >95% is within the range of 35-45 kDa.

2. The compound of claim 1, wherein m is 0.
3. The compound of claim 1, wherein o is 20.
4. The compound of claim 1, wherein n is 4 to 30.
5. The compound of claim 1, wherein n is 4 to 26.
6. The compound of claim 1, wherein n is 23.
7. The compound of claim 1, having the formula:

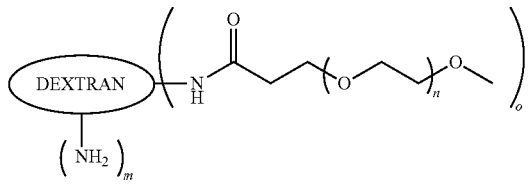

or salt thereof; wherein
m is 0 to 100;
n is 4 to 50; and
o is 2 to 200.

8. The compound of claim 1, having the formula:

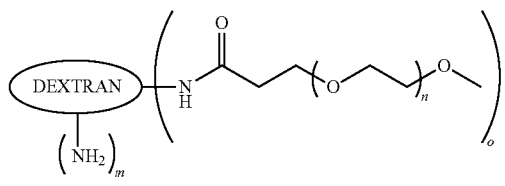

or salt thereof; wherein:
m is 0;
n is 23; and
o is 20.

9. A composition, comprising the compound of claim 1 and a pharmaceutically acceptable carrier.

10. The composition of claim 9, further comprising a PEGylated compound or drug, different from said compound of claim 1.

11. The composition of claim 10, wherein said PEGylated compound or drug different from said compound of claim 1 is one or more of PEGylated antibody, PEGylated enzyme, PEGylated structural protein, PEGylated substrate protein, PEGylated hormone, PEGylated hormone variant, PEGylated hormone biosimilar, PEGylated cytokine, PEGylated lipid, PEGylated liposome, PEGylated synthetic peptide, PEGylated nucleic acid, PEGylated RNA, PEGylated DNA, or a combination thereof.

12. The composition of claim 10, wherein said PEGylated compound or drug different from said compound of claim 1 is one or more of Certolizumab pegol, Phenylalanine ammonia-lyase, Asparaginase, Adenosine deaminase, Uricase, Antihemophilic Factor VIII and variants, Factor IX, Insulin, Erythropoietin, G-CSF, Growth hormone, Growth hormone variant, Interferon beta-1a, Interferon alpha-2a, Interferon alpha 2b, irinotecan hydrochloride trihydrate, doxorubicin HCl liposome, Sulfur hexafluoride-lipid contrast agent, Naloxol, peginesatide, Aptamer, Universal red blood cells, or a combination thereof.

13. The composition of claim 10, wherein the PEGylated compound or drug different from said compound of claim 1 is a PEGylated uricase.

14. The composition of claim 10, wherein the PEGylated compound or drug different from said compound of claim 1 is PEGylated asparaginase.

15. A method of suppressing an anti-PEG IgG or IgM antibody response in a subject in need thereof or at risk thereof, comprising administering to said subject the compound of claim 1.

16. The method of claim 15, further comprising administering a pharmaceutically acceptable carrier.

17. The method of claim 15, further comprising administering a PEGylated compound or drug different from said compound of claim 1.

18. The method of claim 15, wherein the compound of claim 1 crosslinks a subthreshold number of surface immunoglobulin receptors of a B cell in said subject, wherein crosslinking does one or more selected from the group consisting of not activate the B cell, inactivate the B cell, destroy the B cell, or a combination thereof.

UNITED STATES PATENT AND TRADEMARK OFFICE
CERTIFICATE OF CORRECTION

PATENT NO. : 12,390,485 B2
APPLICATION NO. : 17/991925
DATED : August 19, 2025
INVENTOR(S) : Vidal F. de la Cruz et al.

Page 1 of 1

It is certified that error appears in the above-identified patent and that said Letters Patent is hereby corrected as shown below:

In the Claims

At Claim 1, Column 21, Line 26, please delete "formula-OH" and insert therein --formula -OH--.

At Claim 1, Column 21, Line 28, please delete "-COO," and insert therein -- -COO$^-$,--.

At Claim 12, Column 22, Line 35, please delete "beta-la" and insert therein --beta-1a--.

Signed and Sealed this
Twenty-third Day of September, 2025

John A. Squires
*Director of the United States Patent and Trademark Office*